United States Patent [19]

Rubin et al.

[11] Patent Number: 5,747,288
[45] Date of Patent: May 5, 1998

[54] PROTEIN KINASE REQUIRED FOR RAS SIGNAL TRANSDUCTION

[75] Inventors: Gerry Rubin, Berkeley; Marc Therrien, Union City; Henry Chang, Berkeley; Felix Karim, El Cerrito; David Wassarman, San Francisco, all of Calif.

[73] Assignee: The Regents of the University of California, Oakland, Calif.

[21] Appl. No.: 909,983

[22] Filed: Jun. 12, 1997

Related U.S. Application Data

[62] Division of Ser. No. 571,758, Dec. 13, 1995, Pat. No. 5,700,675.
[51] Int. Cl.$^6$ .............................. C12P 21/06; C12N 1/20; C12N 15/00; C07H 21/04
[52] U.S. Cl. ............... 435/69.1; 435/252.3; 435/252.33; 435/320.1; 435/194; 536/23.5; 530/350
[58] Field of Search ................................ 435/69.1, 252.3, 435/252.33, 320.1, 194; 536/23.5; 530/350

[56] References Cited

PUBLICATIONS

Downward et al. Cell. 83 :831–834, Dec. 15, 1995.

*Primary Examiner*—Robert A. Wax
*Assistant Examiner*—Tekchand Saidha
*Attorney, Agent, or Firm*—Richard Aron Osman

[57] ABSTRACT

The kinase suppressor of Ras (Ksr), a novel protein kinase involved in the regulation of cell growth and differentiation, provides an important target for therapeutic intervention. The subject compositions also include nucleic acids which encode a Ksr kinase, and hybridization probes and primers capable of hybridizing with a Ksr gene. Such probes are used to identify mutant Ksr alleles associated with disease. The invention includes methods, including phosphorylation and binding assays, for screening chemical libraries for lead compounds for a pharmacological agent useful in the diagnosis or treatment of disease associated Ksr activity or Ksr-dependent signal transduction.

6 Claims, No Drawings

PROTEIN KINASE REQUIRED FOR RAS SIGNAL TRANSDUCTION

This is a division, of application Ser. No. 08/571,758 filed Dec. 13, 1995, now U.S. Pat. No. 5,700,675.

INTRODUCTION

1. Field of the Invention

The field of the invention is a protein kinase required for Ras signal transduction and its use in pharmaceutical screens.

2. Background

Ras plays a crucial role in diverse cellular processes, such as proliferation and differentiation, where it functions as a nodal point transmitting signals originating from receptor tyrosine kinases (RTKs) to a variety of effector molecules (reviewed in McCormick, 1994a; van der Geer et al., 1994; Burgering and Bos, 1995). Ras activation, which involves a switch from an inactive GDP-bound to an active GTP-bound state, is promoted by a guanine nucleotide-exchange factor. Upon RTK activation, the exchange factor is recruited by an SH2/SH3 domain-containing adaptor molecule to the RTK at the plasma membrane where it can contact and activate Ras. GTP-bound Ras then transmits the signal to downstream effector molecules.

The protein serine/threonine kinase Raf has been identified as a major effector of Ras (reviewed in Daum et al., 1994; McCormick, 1994b). Upon Ras activation, Raf is recruited to the plasma membrane by a direct interaction with Ras, where it is subsequently activated by an unknown mechanism. Raf activation initiates an evolutionarily conserved pathway involving two other kinases, MEK (MAPK Kinase) and MAPK (Mitogen-Activated Protein Kinase) that convey signals to the nucleus through a directional series of activating phosphorylations (reviewed in Marshall, 1994). Although this model for Ras-dependent signal transduction is well-supported, there are still major issues that remain poorly understood. One of them is the mechanism by which Raf is activated. Recent evidence suggests that once recruited to the plasma membrane Raf is activated by phosphorylation (Dent and Sturgill, 1994; Dent et al., 1995). However, a candidate kinase(s) has yet to be identified. Another unresolved issue is the nature of other Ras effectors as well as the pathways they control. Although Raf is clearly a major Ras target, it can not account for all of the cellular responses mediated by Ras (for example see White et al., 1995).

Ectopic expression of an activated Ras1 allele, Ras1$^{V12}$, in the developing Drosophila eye transforms non-neuronal cone cells into R7 photoreceptor cells (Fortini et al., 1992). Similar results are obtained by expression of an activated Drosophila Raf allele, D-Raf$^{Tor4021}$ (Dickson et al., 1992). We carried out a genetic screen designed to isolate mutations that modify the signaling efficiency of Ras1$^{V12}$. Most mutations that decreased the signaling efficiency of Ras1$^{V12}$ also decreased the efficiency of D-RAf$^{Torso4021}$ signaling. However, two groups of mutations were identified that did not alter D-Raf$^{Torso4021}$ signaling. We disclose here the characterization of their respective loci. The Suppressor of Ras1 2-2 (SR2-2) locus encodes a protein homologous to the catalytic subunit of the prenylation enzyme type I geranylgeranyl transferase. We have renamed this locus βGGT-I. The second locus, SR3-1, encodes a novel protein kinase distantly related to Raf kinase members. Based on its sequence and the ability of mutants to reduce Ras1-mediated signaling, we renamed this locus kinase suppressor of ras (ksr). In addition to its function in the Sevenless RTK pathway, we show that ksr is also required for signaling by the Torso RTK. We have isolated mouse and human homologs of ksr. Together, these data indicate that Ksr is an evolutionarily conserved component of the Ras signaling pathway. As such, the human Ksr provides an important target for pharmaceutical intervention.

Relevant Literature

Recent reports on Raf activation include Dent and Sturgill, 1994; Dent et al., 1995; White et al., 1995, Yao et al, 1995; and a recent review by Marshall, 1994.

SUMMARY OF THE INVENTION

The invention provides methods and compositions relating to a novel protein kinase involved in the regulation of cell growth and differentiation: kinase suppressor of Ras (Ksr). As such, the kinase provides an important target for therapeutic intervention. The subject compositions also include nucleic acids which encode a Ksr kinase, and hybridization probes and primers capable of hybridizing with a Ksr gene. Such probes are used to identify mutant Ksr alleles associated with disease.

The invention includes methods for screening chemical libraries for lead compounds for a pharmacological agent useful in the diagnosis or treatment of disease associated Ksr activity or Ksr-dependent signal transduction. In one embodiment, the methods involve (1) forming a mixture comprising a Ksr, a natural intracellular Ksr substrate or binding target such as the 14-3-3 gene product, and a candidate pharmacological agent; (2) incubating the mixture under conditions whereby, but for the presence of said candidate pharmacological agent, said Ksr selectively phosphorylates said substrate or binds said binding target at a control rate; and (3) detecting the presence or absence of a change in the specific phosphorylation of said substrate by said Ksr or phosphorylation or binding of said Ksr to said binding target, wherein such a change indicates that said candidate pharmacological agent is a lead compound for a pharmacological agent capable of modulating Ksr function.

DETAILED DESCRIPTION OF THE INVENTION

A Drosophila melanogaster, a Drosophila virilis, a murine and a human ksr encoding SEQ are set out in SEQUENCE ID NO: 1, 3, 5 and 7, respectively. A Drosophila melanogaster, a Drosophila virilis, a murine and a human ksr protein sequence are set out in SEQ. ID NO: 2, 4, 6 and 8, respectively. Ksr proteins necessarily include a disclosed ksr kinase domain. Hence, Ksr proteins include deletion mutants of natural ksr proteins retaining the ksr kinase domain.

Natural nucleic acids encoding ksr proteins are readily isolated from cDNA libraries with PCR primers and hybridization probes containing portions of the nucleic acid sequence of SEQ. ID NO: 1, 3, 5 and 7. Preferred ksr nucleic acids are capable of hybridizing with one of these sequences under low stringency conditions defined by a hybridization buffer consisting essentially of 1% Bovine Serum Albumin (BSA); 500 mM sodium phosphate (NaPO$_4$); 1 mM EDTA; 7% SDS at a temperature of 42° C. and a wash buffer consisting essentially of 2X SSC (600 mM NaCl; 60 mM Na Citrate); 0.1% SDS at 50° C.; more preferably under low stringency conditions defined by a hybridization buffer consisting essentially of 1% Bovine Serum Albumin (BSA); 500 mM sodium phosphate (NaPO$_4$); 15% formamide; 1 mM EDTA; 7% SDS at a temperature of 50° C. and a wash buffer consisting essentially of 1X SSC (300 mM NaCl; 30 mM Na Citrate); 0.1% SDS at 50° C.; most preferably under low stringency conditions defined by a hybridization buffer consisting essentially of 1% Bovine Serum Albumin (BSA); 200 mM sodium phosphate (NaPO4); 15% formamide; 1 mM EDTA; 7% SDS at a temperature of 50° C. and a wash buffer consisting essentially of 0.5X SSC (150 mM NaCl; 15 mM Na Citrate); 0.1% SDS at 65° C.

The subject nucleic acids are recombinant, meaning they comprise a sequence joined to a nucleotide other than that to which sequence is naturally joined and isolated from a natural environment. The nucleic acids may be part of Ksr-expression vectors and may be incorporated into cells for expression and screening, transgenic animals for functional studies (e.g. the efficacy of candidate drugs for disease associated with expression of a Ksr), etc. These nucleic acids find a wide variety of applications including use as templates for transcription, hybridization probes, PCR primers, therapeutic nucleic acids, etc.; use in detecting the presence of Ksr genes and gene transcripts, in detecting or amplifying nucleic acids encoding additional Ksr homologs and structural analogs, and in gene therapy applications, e.g. using antisense nucleic acids or ribozymes comprising the disclosed Ksr sequences or their complements or reverse complements.

The invention also provides Ksr-specific binding reagents such as antibodies. Such reagents find a wide variety of application in biomedical research and diagnostics. For example, antibodies specific for mutant Ksr allele-products are used to identify mutant phenotypes associated with pathogenesis. Methods for making allele-specific antibodies are known in the art. For example, an mKsr-specific antibody was generated by immunizing mice with a unique N-terminal mKsr peptide (residues 118-249) GST fusion.

The invention provides efficient methods of identifying pharmacological agents or lead compounds for agents active at the level of a Ksr modulatable cellular function, particularly Ksr mediated signal transduction. For example, we have found that a binding complex comprising Ksr, 14-3-3 and Raf exists in stimulated cells; modulators of the stability of this complex effect signal transduction. Generally, the screening methods involve assaying for compounds which interfere with a Ksr activity such as kinase activity or target binding. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target therapeutic indications are limited only in that the target cellular function be subject to modulation, usually inhibition, by disruption of the formation of a complex comprising Ksr and one or more natural Ksr intracellular binding targets including substrates or otherwise modulating Ksr kinase activity. Target indications may include infection, genetic disease, cell growth and regulatory or immunologic dysfunction, such as neoplasia, inflammation, hypersensitivity, etc.

A wide variety of assays for binding agents are provided including labeled in vitro kinase assays, protein-protein binding assays, immunoassays, cell based assays, etc. The Ksr compositions used in the methods are recombinantly produced from nucleic acids having the disclosed Ksr nucleotide sequences. The Ksr may be part of a fusion product with another peptide or polypeptide, e.g. a polypeptide that is capable of providing or enhancing protein-protein binding, stability under assay conditions (e.g. a tag for detection or anchoring), etc.

The assay mixtures comprise one or more natural intracellular Ksr binding targets including substrates, such as the 14-3-3 gene product, or, in the case of an autophosphorylation assay, the Ksr itself can function as the binding target. A Ksr-derived pseudosubstrate may be used or modified (e.g. A to S/T substitutions) to generate effective substrates for use in the subject kinase assays as can synthetic peptides or other protein substrates. Generally, Ksr-specificity of the binding agent is shown by kinase activity (i.e. the agent demonstrates activity of an Ksr substrate, agonist, antagonist, etc.) or binding equilibrium constants (usually at least about $10^6 M^{-1}$, preferably at least about $10^8 M^{-1}$, more preferably at least about $10^9 M^{-1}$). A wide variety of cell-based and cell-free assays may be used to demonstrate Ksr-specific binding; preferred are rapid in vitro, cell-free assays such as mediating or inhibiting Ksr-protein binding, phosphorylation assays, immunoassays, etc.

The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, etc. which may be used to facilitate optimal binding and/or reduce non-specific or background interactions, etc. Also, reagents that otherwise improve the efficiency of the assay, such as protease inhibitors, nuclease inhibitors, antimicrobial agents, etc. may be used.

In a preferred in vitro, binding assay, a mixture of a protein comprising at least one of the conserved Ksr domains, including CA1, CA2, CA3, CA4 and the kinase domain (see Table 1), one or more binding targets or substrates and the candidate agent is incubated under conditions whereby, but for the presence of the candidate pharmacological agent, the Ksr specifically binds the cellular binding target at a first binding affinity or phosphorylates the substrate at a first rate. After incubation, a second binding affinity or rate is detected. Detection may be effected in any convenient way. For cell-free binding assays, one of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components. For example, the label may be detected bound to the solid substrate or a portion of the bound complex containing the label may be separated from the solid substrate, and thereafter the label detected.

The following experiments and examples are offered by way of illustration and not by way of limitation.

EXPERIMENTAL

Mutations in the SR2-2 and SR3-1 loci suppress the eye phenotype of activated Ras I but not that of activated D-Raf.

Ectopic expression of activated Ras1($Ras1^{V12}$) under control of sevenless (sev) promoter/enhancer sequences (sev-$Ras1^{V12}$) transforms cone cells into R7 photoreceptor cells (Fortini et al., 1992). These extra R7 cells disorganize the ommatidial array, which causes a roughening of the external eye surface. The severity of eye roughness appears proportional to the strength of $Ras1^{V12}$-mediated signaling since two copies of the transgene produce a much more disrupted eye than one copy. We took advantage of this sensitized system to conduct a screen for mutations that reduce (suppressors) or increase (enhancers) the degree of eye roughness. We reasoned that a two-fold reduction in the dose of a gene (by mutating one of its two copies) that functions downstream of Ras1 should dominantly alter signaling strength which in turn should visibly modify the roughness of the eye. Based on this assumption, we screened ~200,000 EMS- and ~650,000 X-ray-mutagenized progeny for dominant modifiers of the Ras1$^{V12}$-mediated rough eye phenotype. 18 complementation groups of suppressors with multiple alleles and 13 complementation groups of enhancers of sev-Ras1$^{V12}$ were isolated.

To characterize further the various groups of suppressors, we tested their ability to suppress dominantly the extra R7 cell phenotype caused by overexpression of an activated Drosophila Raf allele (sE-Raf$^{Tor4021}$). Since Raf functions directly downstream of Ras, we expected most of our suppressor groups to modify similarly the sE-Raf$^{Tor4021}$ phenotype. Interestingly, two recessive lethal suppressor groups, SR2-2 and SR3-1 did not reduce the number of extra R7 cells produced by D-Raf$^{Tor4021}$ expression. Scanning electron micrographs of adult eyes illustrate the suppressor phenotypes of one SR3-1 allele. Similar results were obtained with multiple SR2-2 and SR3-1 alleles. We also monitored the suppression of extra R7 cells by counting the number of R7 photoreceptors in cross-sections of adult fly retinae. In wild-type there is one R7 cell per ommatidium, whereas in sev-Ras1$^{V12}$/+ flies we observed 2.3 (n=437) R7 cells per ommatidium. This number was reduced to 1.2 (n=481) R7 cells per ommatidium in sev-Ras1$^{V12}$/+; SR3-1$^{S-638}$/ +flies. In sE-Raf$^{Tor4021}$/+flies, 2.3 (n=302) R7 cells per ommatidium were observed. However, this number remained at 2.3 (n=474) in sE-Raf$^{Tor4021}$/+; SR3-1$^{S-638}$/+flies reflecting the inability of SR3-1 mutations to alter sE-Raf$^{Tor4021}$ signaling strength. Targeting of Ras$^{V12}$ to the plasma membrane by myristylation distinguishes SR2-2 from SR3-1.

Prenylation of the C-terminal CAAX box (C=cysteine, A=aliphatic residue, X=any amino acid) is the major post-translational modification specific to all Ras-like GTPases. When the residue at position "X" is a leucine, as in Ras1, a geranylgeranyl group is added by a type I geranylgeranyl transferase. The addition of this lipidic moiety is required to attach Ras to the plasma membrane (reviewed in Glomset and Farnsworth, 1994). Deletion of the CAAX box abolishes Ras function (Willumsen et al., 1984; Kato et al., 1992), however its activity can be restored if it is brought to the membrane by another localization signal, such as a myristyl group (Buss et al., 1989).

One possibility to account for the ability of a mutant to suppress sev-Ras1$^{V12}$ but not sE-Raf$^{Tor4021}$ is that the locus encodes an enzyme that is required for the membrane localization of Ras1. Consequently, mutations in this locus would not affect D-Raf$^{Tor421}$. To directly test this possibility, we asked if SR2-2 or SR3-1 alleles could suppress activated Ras1 if it is targeted to the membrane by an alternative mechanism. We targeted Ras1$^{V12}$ to the membrane by fusing the first 90 amino acids of Drosophila Src kinase (D-Src; Simon et al., 1985), which contains a myristylation signal, to Ras1$^{V12}$ deleted of its CAAX box (sev-Src90Ras1$^{V12\Delta CAAX}$). While the CAAX box-deleted Ras1$^{V12}$ is inactive, Src90Ras1$^{V12\Delta CAAX}$ produces the same phenotype as Ras1$^{V12}$; that is, it generates extra R7 cells and disrupts the ommatidial array.

We crossed sev-Src90Ras1$^{V12\Delta CAAX}$ flies to SR2-2 and SR3-1 alleles and analyzed the rough eye phenotype. SR2-2$^{S-2110}$ did not suppress the rough eye phenotype while SR3-1$^{S-638}$ suppressed the rough eye phenotype and the production of extra R7 cells. These observations indicate that SR2-2 is involved in prenylation of Ras1 while SR3-1 encodes a component of the Ras1 pathway that is not involved in the process of Ras1 membrane localization.

The SR2-2 locus encodes the Drosophila homolog of the β-subunit of type I geranylgeranyl transferase.

The SR2-2 locus was meiotically mapped to 2–15 (cytological position 25B-C), based on the ability of different mutant alleles to suppress sev-Ras1$^{V12}$. One of the seven recessive lethal SR2-2 alleles recovered contains an X-ray-induced inversion (SR2-2$^{S-2126}$) with a breakpoint at 25B4-6. Genomic DNA spanning this breakpoint was isolated and used to screen a Drosophila eye-antennal imaginal disc cDNA library (see Experimental Procedures). A single class of cDNAs (ranging in size from 0.8 to 1.6 kb) defining a transcription unit disrupted by the inversion present in SR2-2$^{S-226}$, was identified and characterized. Conceptual translation of the longest open reading frame (ORF) defined by these cDNAs predicts a protein of 395 amino acids. Determination of the gene structure by sequencing the corresponding genomic region revealed four exons with the first in-frame methionine located at the beginning of the second exon. The SR2-2$^{S-2126}$ inversion breakpoint maps to the 5'-end of the transcript. Further confirmation that this ORF corresponds to the SR2-2 gene, was provided by sequence analysis of two other mutant alleles, SR2-2$^{S-483}$ and SR2-2$^{S-2554}$, both of which have small deletions that remove the first exon and part of the 5' regulatory sequences. A search of the current protein databases with this ORF indicated that the SR2-2 gene encodes the Drosophila homolog of the catalytic B-subunit of type I geranylgeranyl transferase (βGGT-I) (Marshall, 1993). Sequence alignment with the human and the yeast S. pombe βGGT-I proteins shows a high degree of evolutionary conservation. The human sequence is 44% identical (69% similar) to the Drosophila sequence throughout the entire ORF while the yeast sequence is 36% identical (57% similar) to the Drosophila protein. We therefore renamed this locus, βGGT-I.

The SR3-1 locus encodes a novel protein kinase.

The ability of SR3-1 mutant alleles to suppress the sev-Ras1$^{V12}$ phenotype was meiotically mapped to 347.5, which corresponds to a region near the chromocenter of the third chromosome. The map position was further refined by showing that SR3-1 meiotically maps between two P-elements inserted at 82F8-10 and 83A5-6, respectively. X-ray-induced chromosomal deletions were generated by selecting w$^-$ revertants of one of the P-element insertions. One such deletion, Df(3R)e1025-14, which removes the chromosomal region from 82F8-10 to 83A1-3, complemented the SR3-1-associated lethality. Taken together, these results indicated that the SR3-1 locus lies between 83A1-3, the distal breakpoint of Df(3R)e1025-14, and 83A5-6, the insertion site of P[w$^+$]5E2.

Five overlapping cosmids which cover this chromosomal region were recovered by chromosome walking. To identify restriction site polymorphisms that might have been induced in the SR3-1 alleles, these cosmids were used to probe genomic DNA blots prepared from 9 independent X-ray-induced SR3-1 alleles. Cosmid III revealed polymorphisms in a BamHI restriction digest of two alleles, SR3-1$^{S-69}$ and SR3-1$^{S-511}$. No other cosmid revealed polymorphisms in the 9 tested alleles. A 7 kb SacII genomic fragment which spans the polymorphic BamHI fragments was introduced into the germline by P-element-mediated transformation. This genomic fragment, tested in transgenic flies, rescued both the lethality and the sev-Ras1$^{V12}$-suppression ability of three independent SR3-1 alleles. A single class of cDNAs that was totally encoded by the 7 kb genomic fragment was identified by screening a Drosophila eye-antennal imaginal disc cDNA library and sequenced. The longest cDNA clone represents a transcript of 3.6 kb which is close to the size of a full-length transcript since RNA blot analysis identified a single band of similar size. Sequence analysis of the genomic region revealed that this transcript is encoded by a single exon. Conceptual translation of the longest ORF predicts a protein of 966 amino acids. The presence of an in-frame stop codon upstream of the predicted initiating methionine indicates that this cDNA contains the complete ORF.

A search of current protein databases indicated that SR3-1 encodes a novel protein kinase. The putative catalytic domain, which is C-terminal, contains the characteristic eleven conserved sub-domains found in eukaryotic kinases (Hardie and Hanks, 1995) and is preceded by a long N-terminal region with three distinctive features: a cysteine-rich domain similar to those found in Protein Kinase C isozymes (Hubbard et al., 1991) and Raf kinases (Bruder et al., 1992); four sequences that match the consensus phosphorylation site (PXS/TP) for MAPK (Marshall, 1994); and a block of amino acids rich in serines and threonines followed by a conserved motif (FXFPXXS/T) that resembles the sequence around the Conserved Region 2 (CR2) domain of Raf kinases (Heidecker et al., 1992). Since the SR3-1 locus encodes a putative protein kinase and mutant alleles were isolated as suppressors of sev-Ras1$^{V12}$, we renamed this locus kinase suppressor of ras (ksr).

Further confirmation that this gene corresponds to the ksr (SR3-1) locus was provided by sequencing three ksr alleles which revealed mutations disrupting the Ksr ORF (Table 1).

TABLE 1

Sequence comparison of the Ksr kinases.

TABLE 1-continued

Sequence comparison of the Ksr kinases.

```
                                                                    CA4
                                                        ┌─────────────────────────────────────────────────────────┐
Dm Ksr  t l g k p L H q . . . q h g d s s s p s s s c t s s t p s s p a l f q . . . q R E R E l D Q A G S s . . . . . S S A N L L P T P S L G K h q P s q f n p n v t V t s .           558
Dv Ksr  t l g k p Q L q Q P Q L q h g d s s s p s s s c t s s t p s s p a l f q . . . q Q Q L Q l A T P S A C Q P K P A P A V A A A A T Q Q G q Q s q f n f p n v t L t s I           578
mKsr-1  L T K k E . . H P P A M N . L d s s s N P s s T t s s t p s s p a P f L T S S N P S S A T T P P N P S P G Q R D . . . . . . . . . . . . . . . . . . . . . s R f S f p D I S A C s Q   517
hKsr-1  L T K k E . . H P P A M N h L d s s s N P s s T t s s t p s s p a P f P T S S N P S S A T T P P N P s P G Q R D S R F N F P A A Y F I h H R Q q f I f p D I S A F A H           543 s G G s G g V S l i s n e p V P E Q F P t . A P a T a n g G L D . .           558
Dm Ksr  . . . . . . . . . . . . . . . . . . . . . . s l V s s s n g i M S s s l I g s q T s   N A C N s N A s A A Q T l i s n e p Q A H M A T t E S T L T n g N N N s S   578
Dv Ksr  S N N G S S A N N N S s S S S s C s n g i L H s l T g s q V s T H S A T S Q V S N V S G s   N A s T A a t L t G s l v n s T T T T S T C s f f p r k l s T a g v d k r T p f t   655
mKsr-1  S E A E D D E D E V D D l P s s . . . . . . . . . . . . . . . . . . . . . . . . . .   D D Q P K T D V L G V H E a E a E E P E A G K   517
hKsr-1  S E A E D D . E D E V D D l P s s . . . . . . . . . . . . . . . . . . . . . . . . . .   s e Y t d t h k s n d s d k t v s l s g s a s t d s d r t p v r L d s t e   692
                                                                                      . . s f f p r k l s N a g v d k r V p f t . . r R p W R                 547
                                                                                      . . . . . . . . . . . . . . . . . . . . . . . . r R p W R                 572
                                                                                              T  (S-638)

Dm Ksr  d g d s q q w r q n s i s l k e w d i p y g d l l l e r i g g g r f g t v h r a l w h g d v a v k l l n e d y l g d e h m l e T f r S e v a n f k N t r h e n l v l   655
Dv Ksr  d g d s g q w r q n s i s l k e w d i p y g d l H l e r i g g q g r f g t v h r a l w h g d v a v k l l n e d y l g d e h m l e s f r N e v a n f k K t r h e n l v l   692
mKsr-1  . . . . . . . . . . . q T s V Y l Q e w d i p F E Q V E l G e P i g g q g r W g R v h r G R w h g E v a I R l l E M d G H N Q D h . l K L f K K e v M n Y R Q t r h e n V v l   547
hKsr-1  . . . . . . . . . . . q T s V Y l Q e w d i p F E Q V E l G e P i g g q g r W g R v h r G R w h g E v a I R l l E M d G H N Q D h . l K L f K K e v M n Y R Q t r h e n V v l   572
D-Ral   D A K S s E E N w N i L A E E I l i G P r i g g S g S f g t v Y r a H w h g P v P v K T l n V K T P S P A Q . l Q A f K N e v a M L k K t r h C n I L l
hc-Ral  G Q R D s S Y Y w E i E A S E V M I S T r i g g S g S f g t v Y K C K w h g d v a v k l l K V V D P T P c Q . F Q A f r N e v a V L R K t r h V n I L i
                                                                                                     ▽ (S-721)
                                               I                                              II                                III

Dm Ksr  f m g a c m n p p y l a i v t s l c k g n t l y t y i h q r r e k f a m n   775
Dv Ksr  f m g a c m n p p y l a i v t A l c k g n t l y t y i h q r r e k f a m n   812
mKsr-1  f m g a c m n p P H l a i I t s F c k g R t l H S F V R D P K T S L D I n   658
hKsr-1  f m g a c m n p P H l a i I t s F c k g R t l H S F V R D P K T S L D I n   683
D-Ral   f m g . c V S K p s l a i v t Q W c E g S s l y K H V h V S E T k f K L n   565
hc-Ral  f m g . Y m T K D N l a i v t Q W c E g S s l y K H L h V Q E T k f Q m F   443
               IV                                          V

Dm Ksr  r t l l i a q q i a q g m g y l h a r E i i h k d l r t k n i f i e n g . k v i i t d f g l f s s t k l l y c d m . . . g l g v p h n w l c y l a p e l i r a l q p E
Dv Ksr  r t l l i a q q i a q g m g y l h a r D i i h k d l r t k n i f i e n g . k v i i t d f g l f s s t k l l y c d m . . . g l g v p Q n w l c y l a p e l i r a l q p C
mKsr-1  K t R Q i a q E i I K g m g y l h a K G i V h k d l K S k n V f Y D n g . k v V i t d f g l f G I S G V V R E E R R E N Q l K L S h D w l c y l a p e l V r E M I P G
hKsr-1  K t R Q i a q E i I K g m g y l h a K G i V h k d l K S k n V f Y D n g . k v V i t d f g l f G I S G V V R E G R R E N Q l K L S h D w l c y l a p e l V r E M T P G
D-Ral   T L I D i G R q V a q g m D y l h a K N i i h R d l S v K i G d f g l A T A K T R W S G E K Q A N Q . . p T G S I L W M a p e V i r . . . . . .
hc-Ral  Q L I D i a R q T a q g m D y l h a K N i i h R d M K S N n i f L H E g L T v K i G d f g l A T V K S R W S G S Q Q V E Q . . p T G S V L W M a p e V i r . . . . . .
             VIa                                      VIb                                            VII                                          VIII
```

TABLE 1-continued

Sequence comparison of the Ksr kinases.

```
DmKsr  . e s i i w q v g r . . g m k q s l a n l q s g . . r d v k d l l m l c w t y e k e h r p Q f a r l l s l l e h . . . . . . l p k k r l a r s p s h p v n l s r s a e s v f
DvKsr  . e s i i w q v g r . . g m k q s l a n l q s g . . r d v k d l l m l c w t y e k e h r p D f a r l l s l l e h . . . . . . l p k k r l a r s p s h p v n l s r s a e s v f
mKsr-1 . e A L i w q I g S G E g g V R R V l a S V S L g . . . K E v G E I l S A c w A F D L Q E r p s f S L F M D M l e R . . . . . l p k . . . l N r R L s h p G H F W K s a D I N S
hKsr-1 . e A S i w q I g S G E g m k R V l T S v S L g . . . K E v S E I l S A c w A F D L Q E r p s f S L F M D M l e K . . . . . l p k . . . l N r R L s h p G H F W K s a e L
D-Ral  K D Q i L F M v g r G L . L R P D M S Q V R s D A R r H S k R l A E D c I K y T P K D r p L f R P l l W M l e N M L R T l p k . . . I H r s A s E p . n l T Q s Q L Q N D
hc-Ral R D Q i i F M v g r G Y . A S P D I S K l Y K N C P K A M k R l V A D c V K K V k e E r p L f P Q l l s s I e L L Q H S l p k . . . I N r s A s E p . S l H r A a H T E D
                                                       X                                                                                                IX
```

```
                                                            891
                                                            928
                                                            776
                                                            801
                                                            675
                                                            553
```

```
DmKsr  k p R g e c l e f t P y s d v y s f g t v w y e l i c g e f t f k d q p a
DvKsr  k p P g e c l e f t S y s d v y s f g t v w y e l i c g e f t f k d q p a
mKsr-1 R D E D Q . l P f S K A A d v y A f g t v w y e l Q A R D W P f k H q p a
hKsr-1 k D E D Q . l P f S K A A d v y A f g t v w y e l Q A R D W P L k N q A a
D-Ral  . . M Q e L N P Y S F Q s d v y A f g I v M y e l L A E C L P Y G H I S N
hc-Ral . . M Q D N N P f S F Q s d v y s Y g I v L y e l M T g e L P Y S H I N N
```

```
       S K V M P R F E R F G L G T L E S G N P K M                              966
                                                                              1003
       . . E F L Y L P S P K T P V N F N N F Q F F G S A G N I                   874
       I N A C T L T T S P R L P V F                                             791
                                                                               648
```

Table 1 provides a detailed comparison of the predicted amino acid sequence of Ksr kinases. Conceptual translation of the open reading frame from the longest D. melanogaster (Dm) Ksr cDNA is shown. The positions of mutations in three ksr alleles are indicated: S-548 is a 4 bp X-ray-induced mutation affecting two consecutive codons (CTG-CGA to AGT-GGA). S-638 is an EMS-induced allele that has two separate point mutations changing a GCC codon to GTC and GCG codon to ACG. S-721 is a frameshift mutation due to a 10 bp duplication from adjacent sequences within the codon for asparagine-727. Also shown in the alignment are the conceptual translations of the open reading frames for the Ksr genes from other species: the D. virilis (Dv) Ksr sequence was derived from genomic DNA, the mouse (m) Ksr-1 from a 4 kb cDNA, and the human (h) Ksr-1, deduced from three overlapping cDNA clones (the N-terminal two residues were absent from these clones so the numbering begins with the third residue). The human Ksr is present as one or more of a plurality of alternatively spliced forms, exemplified by Ksr' in the following sequence listing. The amino acid sequences (and their respective positions) for the cysteine-rich regions and the kinase domains of Drosophila (D-Raf) and human (h c-Raf) (Genbank accession number: X07181 and X03484, respectively) are presented. Residues identical to Dm Ksr are lower case. In the N-terminus of the Ksr kinases four Conserved Areas (CA1 to CA4) are boxed. CA1 is a novel domain present only in the Ksr kinases. CA2 is a proline-rich stretch that may represent an SH3-binding site (Alexandropoulos et al., 1995). CA3 is a cysteine-rich stretch, similar to a domain found in multiple signaling molecules. This conserved sequence is also part of the CR1 domain found in Raf kinases (Bruder et al., 1992). CA4 is a long serine/threonine-rich stretch followed by a conserved motif (indicated by a dashed line). This domain resembles the region around the CR2 domain of Raf kinases (Heidecker et al., 1992). The four short thick lines overlying the sequences indicate potential sites of phosphorylation by MAPK (PXS/TP) found in Dm Ksr. The eleven conserved sub-domains characteristic of protein kinases are indicated by roman numerals below their approximate positions.

$ksr^{S-638}$ has two single amino acids changes: alanine-696 to valine and alanine-703 to threonine. The latter substitution alters a highly conserved residue within kinase subdomain II (Hanks et al., 1988). $ksr^{S-721}$ contains a 10 bp insertion in the codon for asparagine-727 within kinase sub-domain III creating a frameshift mutation that truncates the protein at kinase sub-domain III. $ksr^{S-548}$ has a four base pair substitution that changes two consecutive amino acids in the N-terminus of the protein: leucine-50 and arginine-51 to glycine and serine, respectively. Unlike the 16 alleles recovered in the screen which were recessive lethal, $ksr^{S-548}$ produces sub-viable flies which have rough eyes (see below), indicating that it is a weak loss-of-function mutation.

Identification of Ksr homologs in other species defines a novel class of kinases related to Raf kinases.

As a first attempt to determine functionally important domains that comprise the Ksr kinase, we searched for homologs from other species. First, we isolated the complete coding region of ksr from a Drosophila virilis genomic library by low-stringency hybridization (see Experimental Procedures). The D. virilis genomic sequence revealed a single uninterrupted ORF predicting a protein of 1003 amino acids (Table 1). The D. virilis and D. melanogaster Ksr proteins are 96% identical within the kinase domain while the N-terminal region is more divergent (69% identity), although islands of high conservation are present (see Table 1).

A search of translated nucleotide databases (using the TBLASTN program; Altschul et al., 1990) identified a partial ORF derived from a mouse DNA sequence with significant blocks of similarity to the N-terminus of Ksr. This sequence, named hb, had been isolated by Nehls et al. (1994) as part of an exon-trapping strategy to establish the transcription map of a 1 Mb region around the mouse NF1 locus. To determine if the full-length hb transcript also contains a kinase domain related to Ksr, we screened a cDNA library derived from a mouse PCC4 teratocarcinoma cell line with a probe corresponding to the hb sequence (see Experimental Procedures). A 4 kb cDNA clone was isolated and encodes a protein of 873 amino acids that contains a kinase domain highly related to the Ksr kinase domain (51% identity/74% similarity; Table 1). In addition, a human fetal brain cDNA library was screened at low-stringency with the same hb probe (see Experimental Procedures). Thirteen independent cDNA clones were purified and sequenced. They represent partial transcripts ranging in size from 0.6 to 3 kb. Interestingly, they define at least three classes of N-terminal splicing variants. The predicted protein sequence derived from overlapping human cDNA clones is shown in Table 1. With the exception of the first divergent 23 amino acids, which probably represents an alternative exon, human Ksr-1 (hKsr-1) is nearly identical to mouse Ksr-1 (mKsr-1; 95% identity/99% similarity). Subsequent to this analysis, two human Expressed Sequence Tags (GenBank accession numbers: R27352 and 7353) have been reported that correspond to regions of the hKsr kinase domain.

Comparison of mammalian and Drosophila Ksr sequences showed similarity throughout the kinase domain as well as at various locations within the N-terminal region (Table 1). Sequence conservation is obvious within all sub-domains of the kinase domain. Two interesting features are present within sub-domains VIb and VIII. HRDL(K/R/A)XXN (D and N are invariant residues) is the consensus sequence corresponding to sub-domain VIb for the majority of known kinases (Hardie and Hanks, 1995). Instead of an arginine at the second position, a lysine is present for the Ksr homologs which distinguishes them from most other kinases. In addition, the amino acids N-terminal to the APE motif in sub-domain VIII, which have been implicated in substrate recognition specificity, (Hardie and Hanks, 1995) are well-conserved between the Ksr kinases of different species, but differ from those of all other kinases. One peculiarity is found in sub-domain II of the two mammalian proteins. This sub-domain has an invariant lysine residue involved in the phospho-transfer reaction that is conserved in all kinases identified thus far (Hardie and Hanks, 1995), however, both mammalian sequences have an arginine at this position (Table 1). It has been shown that mutagenesis of this lysine residue to any other residue, including arginine, abolishes catalytic function in several kinases (Hanks et al., 1988). However, the sequence conservation between the mouse and the human kinase domains indicates that these enzymes are functional.

Sub-domains VIb and VIII also contain conserved residues that often correlate with hydroxy amino acid recognition (Hanks et al., 1988). For instance, HRDLKXXN (VIb) and T/SXXY/F (VIII) motifs are indicative of Ser/Thr-kinases while HRDLR/AXA/RN (VIb) and PXXW (VIII) motifs are associated with Tyr-kinases. Based solely on these conserved residues it is not clear to which class Ksr kinases belong (Table 1). Indeed, for sub-domain VIb, the Drosophila sequences have an arginine residue at the critical position (like a Tyr-kinase), while the two mammalian sequences have a lysine residue (like a Ser/Thr-kinase). The sub-domain VII motif for all the Ksr members is WXXY, which differs from that found in all other kinases.

In the N-terminal region, four Conserved Areas (CA1 to CA4) can be recognized (Table 1). CA1 is a stretch of 40 amino acids located at the very N-terminus of Ksr kinases and has no equivalent in the database. Its conservation and the identification of a mutation in it (ksr$^{S-548}$) indicate that it plays a role in Ksr function. CA2 is a proline-rich stretch followed by basic residues which may correspond to a class II SH3 -domain binding site (PXXPRXR/K Alexandropoulos et al., 1995), although the two fly sequences diverge from the consensus by one amino acid. CA3 is a cysteine-rich domain similar to the one found in other signaling molecules, such as the CR1 domain of Raf. Finally, CA4 is rich in serines and threonines and also contains a MAPK consensus phosphorylation site.

A search of current databases indicated that the Raf kinase members are the closest relatives to the Ksr kinases based on sequence similarity within the kinase domain (e.g. 42% identity/61% similarity between the Dm Ksr and Raf kinase domains) and shared structural features in the N-terminal region (Table 1). Both the Raf and Ksr kinases have a related C-terminal 300 amino acid kinase domain, named CA5 and CR3, respectively (CR3; Heidecker et al., 1992). The spacing and sizes of the domains of the Ksr kinases are well conserved, except for the presence of an additional ~100 amino acids between the CA4 and CA5 domains of the Drosophila sequences. In addition, they both have a long N-terminal region that contains a cysteine-rich stretch followed by a serine/threonine-rich region, named CA3 and CA4 for Ksr kinases and CR1 and CR2 for Raf kinases. Ksr and Raf kinases also have distinctive features. For instance, the CA1 and CA2 regions found in Ksr kinases are absent from Raf kinases. The Ras-binding domain (RBD) found in the CR1 domain of Raf kinases (Nassar et al., 1995) is absent from Ksr kinases, which suggests that they are regulated differently. Moreover, interaction assays using the yeast two-hybrid system or bacterially-expressed fusion proteins, did not detect any interaction between Ras1 and Ksr, while similar experiments detected an interaction between Ras1 and the CR1 domain of D-Raf. Finally, amino acids in kinase sub-domain VIII, which are important for substrate recognition, are not conserved between Ksr and Raf kinases suggesting that these kinases have different targets. This is supported by the observation that Ksr failed to interact with Dsor1 (D-MEK) in a yeast two-hybrid assay, whereas, D-Raf and Dsor1 interacted strongly.

Ksr functions in multiple RTK pathways.

Recent evidence suggests that RTKs use a similar set of proteins to transduce their signals to the nucleus (see Background). Several lines of genetic evidence suggest that the Ksr kinase corresponds to a new component of this widely used signal transduction pathway. For instance, adult flies homozygous for the sub-viable allele ksr$^{S-548}$ have rough eyes in which ommatidia are missing both outer (R1–R6) and R7 photoreceptor cells. This suggests that, like Ras1 (Simon et al., 1991), ksr has a broader role than just specification of the R7 cell fate. Using the FLP/FRT system (Xu and Rubin, 1993), we did not recover homozygous mutant tissue for the strong allele ksr$^{S-638}$, which indicates that Ksr is required for cell proliferation or survival. In addition, except for the ksr$^{S-548}$ allele, all ksr alleles are recessive lethal and in most cases they die as third instar larvae and lack imaginal discs. This phenotype is often seen with mutations in genes required for cell proliferation (Gatti and Baker, 1989). RNA in situ hybridization showed that ksr MRNA is ubiquitously distributed and is present throughout embryogenesis, consistent with a general role for this kinase.

We directly tested whether ksr is an essential component of the Torso RTK pathway, another Drosophila RTK-dependent signal transduction cascade (reviewed in Duffy and Perrimon, 1994). Torso initiates a signal transduction cascade required for development of the anterior and posterior extremities of the embryo. As for the Sevenless RTK pathway, genetic screens aimed at elucidating this pathway have led to the identification of drk, sos, Ras1 and genes encoding the downstream cassette of kinases (Raf/MEK/MAPK) as being critical for signal propagation (reviewed in Duffy and Perrimon, 1994). This signal transduction cascade appears to control the expression pattern of two genes, tailless (tll) and huckebein (hkb) at the embryonic termini (reviewed in Duffy and Perrimon, 1994). During the cellular blastoderm stage, the posterior domain of expression of both factors depends uniquely on Torso-mediated signaling thereby providing excellent markers of Torso activity.

Embryos derived from mothers homozygous for a torso null mutation have defective termini. The posterior end is missing all structures beyond the seventh abdominal segment, while the anterior end exhibits severe head skeleton defects (reviewed in Duffy and Perrimon, 1994). Consistent with these abnormalities, aberrant expression patterns are observed for tll and hkb; that is, no tll or hkb expression is detected at the posterior end, while tll expression pattern is extended and hkb is retracted at the anterior end. Embryos derived from germlines homozygous for loss-of-function mutations in general RTK components like drk, sos, Ras1 or D-Raf show similar terminal defects, albeit to various degrees, consistent with their role in Torso RTK-mediated signaling (Hou et al., 1995).

To determine ksr acts in the Torso pathway, we used the FLP-FDS system (Hou et al., 1995) to generate ksr germline clones and examined the terminal structures of embryos derived from homozygous mutant oocytes. Like embryos derived from Torso mutant mothers, cuticle preparations of ksr$^{S-638}$ embryos revealed severe terminal defects. They are missing posterior structures beyond the seventh abdominal segment and have collapsed head skeletons. In addition, no tll or hkb expression is detected at the posterior end while a broader domain of tll expression and a reduced one for hkb is observed at the anterior extremity. These results indicate that ksr also functions in the Torso pathway, consistent with Ksr being a general component acting downstream of RTKs.

Activated D-Raf rescues terminal defects observed in embryos derived from germlines homozygous for ksr$^{S-638}$.

The inability of ksr mutants to suppress the sE-Raf$^{Tor4021}$ phenotype in the eye suggested that Ksr functions upstream or in parallel to D-Raf, but not downstream. To clarify where ksr functions relative to D-Raf in the Torso pathway, RNA encoding an activated form of D-Raf (Raf$^{Tor4021}$ was injected into embryos derived from germlines homozygous for ksr$^{S-638}$. If Ksr functions solely upstream of D-Raf then activated D-Raf should rescue the mutant phenotype. In contrast, if Ksr functions solely downstream of D-Raf then injection of activated D-Raf RNA should have no influence on the ksr$^{S-638}$-associated embryonic phenotype. It is also possible that rescue might be observed if Ksr functions in a pathway parallel to D-Raf and can be bypassed by activation of D-Raf to sufficiently high levels. Injection of activated D-Raf partially rescued the ksr$^{S-638}$-associated embryonic terminal defects. These results confirm that Ksr does not act downstream of D-Raf.

Experimental Procedures:

Fly culture and crosses were performed according to standard procedures. Clonal analysis in the eye was performed on the ksr$^{S-638}$ allele (the strongest suppressor of sev-Ras1$^{V12}$ among the ksr alleles) using the FLP/FRT system (Xu and Rubin, 1993).

ksrS-638germline clones were generated as described in Hou et al. (1995). Cuticle preparation of embryos was performed as described in Belvin et al. (1995). In situ hybridization was performed according to Dougan and DiNardo (1992) using digoxigenin-labelled RNA probes. Injection of embryos was performed as described in Anderson and Nüsslein-Volhard (1984). An in vitro trancription kit (Promega) was used to synthesize activated D-Raf RNA the Raf$^{Tor4021}$ DNA template (Dickson et al., 1992).

Scanning electron microscopy was performed as described by Kimmel et al. (1990). Fixation and sectioning of adult eyes were performed as described by Tomlinson and Ready (1987).

The βGGT-I locus was recovered from a chromosome walk initiated by screening a cosmid library (Tamkun et al., 1992) with a genomic fragment flanking a P-element [1(2)05714] inserted at 25B4-6 (Karpen and Spradling, 1992; Berkeley Drosophila Genome Project, pers. comm.). A 1.7 kb SpeI-SpI genomic fragment spanning the S-2126 allele inversion breakpoint was used to screen a Drosophila eye-antennal imaginal disc cDNA library in λgt10. Sixteen related cDNA clones were isolated from ~700,000 pfu screened.

The ksr gene was isolated from a chromosome walk. Genomic blot analysis of X-ray-induced ksr alleles was performed according to standard procedures (Sambrook et al., 1989). The 2.9 kb and 2.2 kb BamHI fragments from cosmid III identified polymorphisms in the S-69 and S-511 alleles, respectively. A 7 kb EcoRI genomic fragment encompassing all of the 2.9 kb BamHI fragment and part of the 2.2 kb BamHI fragment was used along with the 2.2 kb BamHI fragment to screen ~700,000 phage from a Drosophila eye-antennal imaginal disc cDNA library in λgt10. Seven related cDNA clones were isolated and characterized by sequencing.

A D. virilis genomic library was screened at reduced stringency using the Dm Ksr kinase domain as a probe. In brief, filters were hybridized in 5X SSCP; 10X Denhart; 0.1% SDS; 200 μg/ml sonicated salmon sperm DNA at 42° C. for 12 hrs, rinsed several times at room temperature and washed twice for 2 hrs at 50° C. in 1X SSC; 0.1% SDS. 12 genomic clones were identified; one was purified and analyzed by sequencing.

A DNA fragment corresponding to the hb DNA sequence was prepared by PCR from a mouse brain cDNA library and used as a probe to screen a mouse PCC4 teratocarcinoma cDNA library (Stratagene). One fill-length cDNA clone, named mKsr-1, was obtained from 1×10$^6$ pfu screened. Using the mKsr-1 kinase domain as a probe, 1×10$^6$ pfu of a human fetal brain cDNA library (Clontech) was hybridized at reduced stringency (see above). Thirteen related cDNA clones were isolated and characterized by sequencing. They all represent partial transcripts and only one of them, named hKsr- 1, has a complete kinase domain.

DNA sequences were performed by the dideoxy chain termination procedure (Sanger et al., 1977) using the Automated Laser Fluorescence (ALF) system (Pharmacia). Templates were prepared by sonicating plasmid DNA and inserting the sonicated DNA into the M13mp10 vector. The entire coding regions of βGGT-I and Ksr cDNAs from each species were sequenced on both strands as well as the genomic regions that correspond to the βGGT-1 and Dm ksr loci. Sequences were analysed using the Staden (R. Staden, MRC of Molecular Biology, Cambridge UK) and the Genetics Computer Group, Inc. software packages. The chromosomal regions for different βGGT-I and ksr mutant alleles were cloned into the λ_ZAP-express vector (Stratagene) and their respective coding regions were completely sequenced using oligonucleotide primers.

Cited References

Alexandropoulos, K., et al. (1995).Proc. Natl. Acad. Sci. USA 92, 3110–3114.
Altschul, S. F., et al. (1990) J. Mol. Biol. 215, 403–410.
Anderson, K. V. and Nüsslein-Volhard, C. (1984). Nature 311, 223–227.
Belvin, M. P., Jin, Y. and Anderson, K. V. (1995). Genes Dev. 9, 783–793.
Bier, E., et al. (1989). Genes Dev. 3, 1273–1287.
Bruder, J. T., Heidecker, B. and Rapp, U. R. (1992). Genes Dev. 6, 545–556.
Burgering, B. M. T. and Bos, J. L. (1995). Trends Biochem. Sci. 20, 18–22.
Buss, J. E., et al. (1989). Science 243, 1600–1603.
Cano, E. and Mahadevan, L. C. (1995). Trends Biochem. Sci. 20, 117–122.
Daum, G., et al. (1994). Trends Biochem. Sci. 19, 474–480.
Dent, P., et al. (1995). Science 268, 1902–1906.
Dent, P. and Sturgill, T. W. (1994). Proc. Natl. Acad. Sci. USA 91, 9544–9548.
Dickson, B., et al. (1992), Nature 360, 600–603.
Dougan, S. and DiNardo, S. (1992). Nature 360, 347–350.
Duffy, J. B. and Perrimon, N. (1994). Dev. Biol. 166, 380–395.
Fortini, M. E., Simon, M. A. and Rubin, G. M. (1992). Nature 355, 559–561.
Gatti, M. and Baker, B. S. (1989). Genes Dev. 3, 438–453.
Glomset, J. A. and Farnsworth, C. C. (1994). Annu. Rev. Cell Biol. 10, 181–205.
Hanks, S. K., Quinn, A. M. and Hunter, T. (1988). Science 241, 42–52.
Hardie, Gand Hanks, S. Eds. (1995). The protein kinase (part I): protein-serine kinases. (Facts Book Series, Academic Press inc.).
Heidecker, G., Kolch, W., Morrison, D. K. and Rapp, U. R. (1992). Adv. Can. Res. 58, 53–73.
Hou, X. S., Chou, T. B., Melnick, M. B. and Perrimon, N. (1995). Cell 81, 63–71.
Hubbard, S. R., et al. (1991). Science 254, 1776–1779.
Karpen, G. H. and Spradling, A. C. (1992). Genetics 132, 737–753.
Kato, K., et al. (1992). Proc. Natl. Acad. Sci. USA 89, 6403–6407.
Kimmel, B. E., Heberlein, U. and Rubin, G. M. (1990). Genes Dev. 4, 712–727.
Marshall, C. J. (1993). Science:259, 1865–1866.
Marshall, C. J. (1994). Curr. Opin. Genet. Dev. 4, 82–89.
McCormick, F. (1994a). Curr. Opin. Genet. Dev. 4, 71–76.
McCormick, F. (1994b). Trends Cell Biol. 4, 347–350.
Nassar, N., et al. (1995). Nature 375, 554–560.
Nehls, M., et al. (1994) (Genbank accession number X81634)
Sambrook, J., Fritsch, E. F. and Maniatis, T. (1989). Molecular Cloning: A Laboratory Manual, Second Edition (Cold Spring Harbor, New York: Cold Spring Harbor Laboratory Press).
Sanger, F., Nicklen, S. and Coulson, A. (1977). Proc. Natl. Acad. Sci. USA 74, 5463–5467.
Sidow, A. and Thomas, W. K. (1994) Curr. Biol. 4, 596–603.
Simon, M. A., et al. (1991). Cell 67, 701–716.

Simon, M. A., et al. (1985). Cell 42, 831–840.
Tamkun, J. W., et al. (1992). Cell 68, 561–572.
Tomlinson, A. and Ready, D. F. (1987). Dev. Biol. 123, 264–275.
van der Geer, P., et al. (1994). Annu. Rev. Cell Biol. 10, 251–337.
White, M. A., et al. (1995). Cell 80, 533–541.
Willumsen, B. M., et al. (1984). EMBO J. 3, 2581–2585.
Xu, T. and Rubin, G. M. (1993). Development 117, 1223–1237.

Pharmaceutical lead compound screening assays.

1. Protocol for Ksr—substrate phosphorylation assay.

A. Reagents:
Neutral Avidin: 20 µg/ml in PBS.
hKsr: $10^{-8}$–$10^{-5}$M hKsr at 20 µg/ml in PBS.
Blocking buffer: 5% BSA, 0.5% Tween 20 in PBS; 1 hour at room temperature.
Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
[$^{32}$P]λ-ATP 10x stock: $2\times10^{-5}$M cold ATP with 100 µCi [$^{32}$P]λ-ATP. Place in the 4° C. microfridge during screening.
Substrate: $2\times10^{-6}$M biotinylated synthetic peptide kinase substrate (MBP, Sigma) at 20 µg/ml in PBS.
Protease inhibitor cocktail (1000X): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB #917575), and 2mM NaVo$_3$ (Sigma #S-6508) in 10 ml of PBS.

B. Preparation of assay plates:
Coat with 120 µl of stock Neutralite avidin per well overnight at 4° C.
Wash 2 times with 200 µl PBS.
Block with 150 µl of blocking buffer.
Wash 2 times with 200 µl PBS.

C. Assay:
Add 40 µl assay buffer/well.
Add 40 µl hKsr (0.1–10 pmoles/40 ul in assay buffer)
Add 10 µl compound or extract.
Shake at 30° C. for 15 minutes.
Add 10 µl [$^{32}$P]λ-ATP 10x stock.
Add 10 µl substrate.
Shake at 30° C. for 15 minutes.
Incubate additional 45 minutes at 30° C.
Stop the reaction by washing 4 times with 200 µl PBS.
Add 150 µl scintillation cocktail.
Count in Topcount.

D. Controls for all assays (located on each plate):
a. Non-specific binding (no hKsr added)
b. cold ATP to achieve 80% inhibition.

2. Protocol for hKsr—Raf binding assay.

A. Reagents:
Anti-myc antibody: 20 µg/ml in PBS.
Blocking buffer: 5% BSA, 0.5% Tween 20 in PBS; 1 hour at room temperature.
Assay Buffer: 100 mM KCl, 20 mM HEPES pH 7.6, 0.25 mM EDTA, 1% glycerol, 0.5% NP-40, 50 mM P-mercaptoethanol, 1 mg/ml BSA, cocktail of protease inhibitors.
$^{32}$P hKsr 10x stock: $10^8$–$10^6$ M "cold" hKsr (full length) supplemented with 200,000–250,000 cpm of labeled hKsr (HMK-tagged) (Beckman counter). Place in the 4° C. microfridge during screening.
Protease inhibitor cocktail (1000X): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB #917575), and 2mM NaVo$_3$ (Sigma #S-6508) in 10 ml of PBS.
Raf: $10^{-8}$–$10^{-5}$M myc eptitope-tagged Raf in PBS.

B. Preparation of assay plates:
Coat with 120 µl of stock anti-myc antibody per well overnight at 4° C.
Wash 2X with 200 µl PBS.
Block with 150 µl of blocking buffer.
Wash 2X with 200 µl PBS.

C. Assay:
Add 40 µl assay buffer/well.
Add 10 µl compound or extract.
Add 10 µl $^{33}$P-hKsr (20,000–25,000 cpm/0.1–10 pmoles/well=$10^{-9}$–$10^{-6}$M final concentration).
Shake at 25° C. for 15 minutes.
Incubate additional 45 minutes at 25° C.
Add 40 µl eptitope-tagged Raf (0.1–10 pmoles/40 ul in assay buffer)
Incubate 1 hour at room temperature.
Stop the reaction by washing 4 times with 200 µl PBS.
Add 150 µl scintillation cocktail.
Count in Topcount.

D. Controls for all assays (located on each plate):
a. Non-specific binding (no hKsr added)
b. Soluble (non-tagged Raf) to achieve 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid encoding a kinase suppressor of ras (Ksr) protein.

2. An isolated nucleic acid according to claim 1, which specifically hybidizes with a nucleic acid consisting of the sequence defined by SEQ ID NO: 1, 3, 5, or 7 under low stringency conditions.

3. An isolated nucleic acid having a sequence defined by or complementary or reverse complementary to SEQ ID NO:1, 3, 5 or 7.

4. A vector comprising a nucleic acid according to claim 2 operably linked to a transcription regulatory region not naturally lined to a Ksr-encoding gene.

5. A host cell comprising a vector according to claim 4.

6. A method of making a Ksr protein, said method comprising incubating a cell according to claim 5.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 3697 base pairs
( B ) TYPE: nucleic acid
( C ) STRANDEDNESS: double ( D ) TOPOLOGY: linear ( i i ) MOLECULE TYPE: cDNA ( x i ) SEQUENCE DESCRIPTION: SEQ ID NO:1:

```
GAATTCCAAT TATTGCTTTT TCGCATTGCC TAAGCCGTTT AGAGTTGCGG GCGTTAGCGT     60
GCGCGATAGC CGGAGCACCG AACGTCAAGG TCGCTTGGCG AGGGCACAA TGCGGGGCGG    120
AGTCCCAGCC ATTGGTCCCA TCGAATCGTC GAGTCCCCGA GAGGGCGTCT GAAAAAATCA   180
ATCGGGCTCC ACTCCGTCGC GAATAAGCAG GATGAGCAGC AACAACAACG CACCCGCATC   240
GGCTCCAGAC ACGGGCTCCA CCAATGCCAA CGATCCCATC TCCGGTTCGC TGTCCGTAGA   300
CAGCAACCTG GTTATCATTC AGGACATGAT TGATCTCTCG GCCAACCATC TGGAGGGCCT   360
GCGAACGCAG TGCGCGATCA GCTCCACGCT GACGCAGCAG GAGATTCGTT GCCTGGAGTC   420
GAAGCTGGTG CGATACTTCT CCGAGCTGCT GCTGGCGAAG ATGCGGCTAA ATGAGCGCAT   480
CCCGGCCAAC GGGCTTGTGC CCACACAAC GGGCAACGAA CTGAGGCAAT GGCTGCGCGT    540
AGTGGGCCTT AGCCAGGGGA CTCTTACCGC CTGCCTTGCT CGCCTGACCA CTCTAGAGCA   600
AAGCCTGCGT CTCAGCGACG AGGAGATCCG TCAACTCCTG GCTGACAGCC CCAGCCAGCG   660
AGAGGAGGAG GAACTGCGAC GCCTGACCAG GGCCATGCAG AACTTAAGGA AGTGCATGGA   720
GTCGCTGGAG AGCGGTACTG CGGCTAGCAA CAACGATCCA GAGCAGTGGC ACTGGGACTC   780
CTGGACAGG CCCACCCACA TTCATCGCGG CAGTGTGGGA AACATTGGAC TGGGTAACAA    840
TTCAACCGCC TCCCCGAGAA CCCATCATCG CCAGCATGGT GTCAAGGGAA AGAATTCCGC   900
TCTGGCCAAC TCCACCAACT TCAAAAGTGG CCGCCAATCG CCCTCAGCGA CAGAAGAGCT   960
GAACAGCACA CAGGGTTCCC AGCTGACTTT AACCCTTACG CCCTCGCCAC CCAATTCGCC  1020
CTTCACGCCT TCCAGTGGGC TGAGCAGCAG CCTTAATGGA ACACCACAGA GGAGTCGTGG  1080
TACCCCGCCG CCAGCCAGAA AGCACCAGAC CTTGCTGAGC CAGAGTCATG TGCAAGTGGA  1140
CGGGGAGCAA TTAGCCCGCA ACCGTTTGCC CACTGATCCC AGCCCGATA GCCACAGCTC   1200
CACCAGCTCG GACATCTTTG TGGACCCAAA TACTAATGCC AGCTCCGGAG GAAGTTCCTC  1260
GAACGTGCTT ATGGTGCCAT GCTCTCCGGG CGTGGGTCAC GTGGGCATGG GTCATGCAAT  1320
CAAGCATCGT TTCACCAAGG CCCTGGGCTT CATGGCCACC TGTACCCTGT GCCAGAAGCA  1380
GGTCTTTCAC CGCTGGATGA AGTGCACCGA CTGCAAGTAC ATCTGCCACA AGTCATGCGC  1440
ACCGCACGTA CCGCCCTCCT GTGGACTTCC ACGAGAATAT GTGGACGAGT TCGGCACAT   1500
AAAGGAGCAG GGAGGATACG CCAGTCTGCC GCATGTGCAT GGCGCGGCGA AAGGATCCCC  1560
TTTGGTAAAA AAGAGCACCC TGGGTAAGCC CTTGCATCAG CAGCACGGCG ATAGCAGTTC  1620
GCCGAGTTCC AGCTGCACTA GTTCCACGCC CAGCAGTCCG GCGCTGTTCC AGCAAAGGGA  1680
GCGCGAGCTG GATCAGGCGG GCAGCAGCTC TAGCGCCAAT CTGTTACCTA CGCCTTCGCT  1740
TGGCAAGCAC CAGCCGAGTC AATTCAACTT TCCCAACGTG ACGGTGACGA GCAGTGGCGG  1800
AAGCGGTGGT GTATCGCTCA TCTCCAATGA ACCAGTGCCA GAGCAATTCC CCACGGCGCC  1860
TGCAACAGCC AACGGAGGAC TTGATAGTCT GGTGAGCAGC TCCAACGGGC ACATGAGCTC  1920
GCTCATCGGT AGCCAAACTT CAAACGCTTC TACTGCGGCC ACCTTGACGG GCAGTCTGGT  1980
CAATAGCACA ACCACCACCA GCACCTGCAG TTTCTTTCCG CGAAAATTGA GCACAGCCGG  2040
TGTGGATAAG AGGACGCCGT TCACCAGCGA GTGCACGGAT ACCCACAAGT CAAATGACAG  2100
CGACAAGACA GTCTCCTTGT CTGGAAGTGC CAGCACGGAC TCGGACCGGA CACCCGTTCG  2160
TGTGGATTCA ACGGAAGACG GAGACTCGGG ACAATGGCGA CAGAACTCGA TCTCACTCAA  2220
```

```
GGAATGGGAC ATCCCGTATG GTGATCTGCT TCTGCTCGAG CGGATAGGGC AGGGACGCTT    2280

CGGCACCGTG CATCGAGCCC TTTGGCACGG AGATGTGGCG GTTAAGCTGC TCAACGAGGA    2340

CTATCTGCAA GACGAACACA TGCTGGAGAC GTTTCGCAGC GAGGTAGCCA ACTTCAAGAA    2400

CACTCGACAC GAGAACCTGG TGCTGTTCAT GGGAGCCTGC ATGAACCCAC CATATTTGGC    2460

CATTGTGACT TCATTGTGCA AGGGCAACAC CTTGTATACG TATATTCACC AGCGTCGGGA    2520

GAAGTTTGCC ATGAACCGGA CTCTCCTCAT TGCCCAGCAG ATCGCCCAGG GCATGGGCTA    2580

CCTGCACGCA AGGGAGATCA TCCACAAAGA TCTGCGCACC AAGAACATCT TCATCGAGAA    2640

CGGCAAGGTG ATTATCACGG ACTTTGGGCT GTTCAGCTCC ACCAAGCTGC TCTACTGTGA    2700

TATGGGCCTA GGAGTGCCCC ACAACTGGTT GTGCTACCTG GCGCCGGAGC TAATCCGAGC    2760

ATTGCAGCCG GAGAAGCCGC GTGGAGAGTG TCTGGAGTTC ACCCCATACT CCGATGTCTA    2820

CTCTTTCGGA ACCGTTTGGT ACGAGCTAAT CTGCGGCGAG TTCACATTCA AGGATCAGCC    2880

GGCGGAATCG ATCATCTGGC AGGTTGGCCG TGGGATGAAG CAGTCGCTGG CCAACCTGCA    2940

GTCTGGACGG GATGTCAAGG ACTTGCTGAT GCTGTGCTGG ACCTACGAGA AGGAGCACCG    3000

GCCGCAGTTC GCACGCCTGC TCTCCCTGCT GGAGCATCTT CCCAAGAAGC GTCTGGCGCG    3060

CAGTCCCTCC CACCCCGTCA ACCTTTCCCG TTCCGCCGAG TCCGTGTTCT GAGGGAACTG    3120

CAGCATGGCC ACTGTCACTG TCTAGTACAA TTTCGATCTA CCAACTAAGC TAGCTCGCTT    3180

TGTGCCCTCG TCCACTCTAC ACAAACTCTC TCCCAAGGCG AAGTTCTATC GAGCCGAGCG    3240

AAGATTGTAA ATACATAAAC GTAACTACCA AATTATAGCA ATCCATTTTA AAAACTACAT    3300

ACATATGTGT AGGCATGTAT CGGGAGCACT CCAGTTGCAG TTGTTAGCAA ACGAAACAAA    3360

GGCAAATCAA ATGTTAACTC GAAAAGACA AAACGCTTAA ATGTTAAGA GCAGAGGCAA     3420

ACAGAGAAGG CATAGACATA CATATACAAA CAAACAAACA AGCACTGTGG CAAACATAAA    3480

TGTAAACGTT AATCAGGTGA GCAATTTCTA AATTGTTAAT TATGTGTAAG AGAACTATAT    3540

ATATATATAT ATATATATAT ATATATATAT ATATACATGT ATATACAGCA GCAATGTATT    3600

GTATATGACG GACTAGTGTT AAATTAAATA TATATTGTGA ATTATGTATG GTCAAGTGTA    3660

TATAGTAAAT GGACTTTAAA TGCGAAATCG GGAATTC                            3697
```

( 2 ) INFORMATION FOR SEQ ID NO:2:

( i ) SEQUENCE CHARACTERISTICS:
        ( A ) LENGTH: 966 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:2:

```
Met Ser Ser Asn Asn Asn Ala Pro Ala Ser Ala Pro Asp Thr Gly Ser
 1               5                  10                  15

Thr Asn Ala Asn Asp Pro Ile Ser Gly Ser Leu Ser Val Asp Ser Asn
            20                  25                  30

Leu Val Ile Ile Gln Asp Met Ile Asp Leu Ser Ala Asn His Leu Glu
        35                  40                  45

Gly Leu Arg Thr Gln Cys Ala Ile Ser Ser Thr Leu Thr Gln Gln Glu
    50                  55                  60

Ile Arg Cys Leu Glu Ser Lys Leu Val Arg Tyr Phe Ser Glu Leu Leu
65                  70                  75                  80

Leu Ala Lys Met Arg Leu Asn Glu Arg Ile Pro Ala Asn Gly Leu Val
                85                  90                  95
```

```
Pro His Thr Thr Gly Asn Glu Leu Arg Gln Trp Leu Arg Val Gly
        100                 105                 110
Leu Ser Gln Gly Thr Leu Thr Ala Cys Leu Ala Arg Leu Thr Thr Leu
        115                 120                 125
Glu Gln Ser Leu Arg Leu Ser Asp Glu Glu Ile Arg Gln Leu Leu Ala
        130                 135                 140
Asp Ser Pro Ser Gln Arg Glu Glu Glu Glu Leu Arg Arg Leu Thr Arg
145                     150                 155                 160
Ala Met Gln Asn Leu Arg Lys Cys Met Glu Ser Leu Glu Ser Gly Thr
                165                 170                 175
Ala Ala Ser Asn Asn Asp Pro Glu Gln Trp His Trp Asp Ser Trp Asp
                180                 185                 190
Arg Pro Thr His Ile His Arg Gly Ser Val Gly Asn Ile Gly Leu Gly
                195                 200                 205
Asn Asn Ser Thr Ala Ser Pro Arg Thr His His Arg Gln His Gly Val
210                     215                 220
Lys Gly Lys Asn Ser Ala Leu Ala Asn Ser Thr Asn Phe Lys Ser Gly
225                     230                 235                 240
Arg Gln Ser Pro Ser Ala Thr Glu Glu Leu Asn Ser Thr Gln Gly Ser
                245                 250                 255
Gln Leu Thr Leu Thr Leu Thr Pro Ser Pro Pro Asn Ser Pro Phe Thr
                260                 265                 270
Pro Ser Ser Gly Leu Ser Ser Ser Leu Asn Gly Thr Pro Gln Arg Ser
                275                 280                 285
Arg Gly Thr Pro Pro Pro Ala Arg Lys His Gln Thr Leu Leu Ser Gln
        290                 295                 300
Ser His Val Gln Val Asp Gly Glu Gln Leu Ala Arg Asn Arg Leu Pro
305                     310                 315                 320
Thr Asp Pro Ser Thr Asp Ser His Ser Ser Thr Ser Ser Asp Ile Phe
                        325                 330                 335
Val Asp Pro Asn Thr Asn Ala Ser Ser Gly Gly Ser Ser Ser Asn Val
                340                 345                 350
Leu Met Val Pro Cys Ser Pro Gly Val Gly His Val Gly Met Gly His
                355                 360                 365
Ala Ile Lys His Arg Phe Thr Lys Ala Leu Gly Phe Met Ala Thr Cys
        370                 375                 380
Thr Leu Cys Gln Lys Gln Val Phe His Arg Trp Met Lys Cys Thr Asp
385                 390                 395                     400
Cys Lys Tyr Ile Cys His Lys Ser Cys Ala Pro His Val Pro Pro Ser
                405                 410                 415
Cys Gly Leu Pro Arg Glu Tyr Val Asp Glu Phe Arg His Ile Lys Glu
                420                 425                 430
Gln Gly Gly Tyr Ala Ser Leu Pro His Val His Gly Ala Ala Lys Gly
        435                 440                 445
Ser Pro Leu Val Lys Lys Ser Thr Leu Gly Lys Pro Leu His Gln Gln
        450                 455                 460
His Gly Asp Ser Ser Ser Pro Ser Ser Ser Cys Thr Ser Ser Thr Pro
465                 470                 475                 480
Ser Ser Pro Ala Leu Phe Gln Gln Arg Glu Arg Glu Leu Asp Gln Ala
                485                 490                 495
Gly Ser Ser Ser Ser Ala Asn Leu Leu Pro Thr Pro Ser Leu Gly Lys
                500                 505                 510
His Gln Pro Ser Gln Phe Asn Phe Pro Asn Val Thr Val Thr Ser Ser
```

|     |     |     |     |     | 515 |     |     |     |     | 520 |     |     |     |     | 525 |     |     |     |
| --- | --- | --- | --- | --- | --- | --- | --- | --- | --- | --- | --- | --- | --- | --- | --- | --- | --- | --- |
| Gly | Gly | Ser | Gly | Gly | Val | Ser | Leu | Ile | Ser | Asn | Glu | Pro | Val | Pro | Glu |
| 530 |     |     |     |     | 535 |     |     |     |     | 540 |     |     |     |     |     |
| Gln | Phe | Pro | Thr | Ala | Pro | Ala | Thr | Ala | Asn | Gly | Gly | Leu | Asp | Ser | Leu |
| 545 |     |     |     |     | 550 |     |     |     |     | 555 |     |     |     |     | 560 |
| Val | Ser | Ser | Ser | Asn | Gly | His | Met | Ser | Ser | Leu | Ile | Gly | Ser | Gln | Thr |
|     |     |     |     | 565 |     |     |     |     | 570 |     |     |     |     | 575 |     |
| Ser | Asn | Ala | Ser | Thr | Ala | Ala | Thr | Leu | Thr | Gly | Ser | Leu | Val | Asn | Ser |
|     |     |     | 580 |     |     |     |     | 585 |     |     |     |     | 590 |     |     |
| Thr | Thr | Thr | Thr | Ser | Thr | Cys | Ser | Phe | Phe | Pro | Arg | Lys | Leu | Ser | Thr |
|     |     | 595 |     |     |     |     | 600 |     |     |     |     | 605 |     |     |     |
| Ala | Gly | Val | Asp | Lys | Arg | Thr | Pro | Phe | Thr | Ser | Glu | Cys | Thr | Asp | Thr |
|     | 610 |     |     |     |     | 615 |     |     |     |     | 620 |     |     |     |     |
| His | Lys | Ser | Asn | Asp | Ser | Asp | Lys | Thr | Val | Ser | Leu | Ser | Gly | Ser | Ala |
| 625 |     |     |     |     | 630 |     |     |     |     | 635 |     |     |     |     | 640 |
| Ser | Thr | Asp | Ser | Asp | Arg | Thr | Pro | Val | Arg | Val | Asp | Ser | Thr | Glu | Asp |
|     |     |     |     | 645 |     |     |     |     | 650 |     |     |     |     | 655 |     |
| Gly | Asp | Ser | Gly | Gln | Trp | Arg | Gln | Asn | Ser | Ile | Ser | Leu | Lys | Glu | Trp |
|     |     |     | 660 |     |     |     |     | 665 |     |     |     |     | 670 |     |     |
| Asp | Ile | Pro | Tyr | Gly | Asp | Leu | Leu | Leu | Glu | Arg | Ile | Gly | Gln | Gly |
|     |     | 675 |     |     |     |     | 680 |     |     |     |     | 685 |     |     |     |
| Arg | Phe | Gly | Thr | Val | His | Arg | Ala | Leu | Trp | His | Gly | Asp | Val | Ala | Val |
|     | 690 |     |     |     |     | 695 |     |     |     |     | 700 |     |     |     |     |
| Lys | Leu | Leu | Asn | Glu | Asp | Tyr | Leu | Gln | Asp | Glu | His | Met | Leu | Glu | Thr |
| 705 |     |     |     |     | 710 |     |     |     |     | 715 |     |     |     |     | 720 |
| Phe | Arg | Ser | Glu | Val | Ala | Asn | Phe | Lys | Asn | Thr | Arg | His | Glu | Asn | Leu |
|     |     |     |     | 725 |     |     |     |     | 730 |     |     |     |     | 735 |     |
| Val | Leu | Phe | Met | Gly | Ala | Cys | Met | Asn | Pro | Pro | Tyr | Leu | Ala | Ile | Val |
|     |     |     | 740 |     |     |     |     | 745 |     |     |     |     | 750 |     |     |
| Thr | Ser | Leu | Cys | Lys | Gly | Asn | Thr | Leu | Tyr | Thr | Tyr | Ile | His | Gln | Arg |
|     |     | 755 |     |     |     |     | 760 |     |     |     |     | 765 |     |     |     |
| Arg | Glu | Lys | Phe | Ala | Met | Asn | Arg | Thr | Leu | Leu | Ile | Ala | Gln | Gln | Ile |
| 770 |     |     |     |     | 775 |     |     |     |     | 780 |     |     |     |     |     |
| Ala | Gln | Gly | Met | Gly | Tyr | Leu | His | Ala | Arg | Glu | Ile | Ile | His | Lys | Asp |
| 785 |     |     |     |     | 790 |     |     |     |     | 795 |     |     |     |     | 800 |
| Leu | Arg | Thr | Lys | Asn | Ile | Phe | Ile | Glu | Asn | Gly | Lys | Val | Ile | Ile | Thr |
|     |     |     |     | 805 |     |     |     |     | 810 |     |     |     |     | 815 |     |
| Asp | Phe | Gly | Leu | Phe | Ser | Ser | Thr | Lys | Leu | Leu | Tyr | Cys | Asp | Met | Gly |
|     |     |     | 820 |     |     |     |     | 825 |     |     |     |     | 830 |     |     |
| Leu | Gly | Val | Pro | His | Asn | Trp | Leu | Cys | Tyr | Leu | Ala | Pro | Glu | Leu | Ile |
|     |     | 835 |     |     |     |     | 840 |     |     |     |     | 845 |     |     |     |
| Arg | Ala | Leu | Gln | Pro | Glu | Lys | Pro | Arg | Gly | Glu | Cys | Leu | Glu | Phe | Thr |
| 850 |     |     |     |     | 855 |     |     |     |     | 860 |     |     |     |     |     |
| Pro | Tyr | Ser | Asp | Val | Tyr | Ser | Phe | Gly | Thr | Val | Trp | Tyr | Glu | Leu | Ile |
| 865 |     |     |     |     | 870 |     |     |     |     | 875 |     |     |     |     | 880 |
| Cys | Gly | Glu | Phe | Thr | Phe | Lys | Asp | Gln | Pro | Ala | Glu | Ser | Ile | Ile | Trp |
|     |     |     |     | 885 |     |     |     |     | 890 |     |     |     |     | 895 |     |
| Gln | Val | Gly | Arg | Gly | Met | Lys | Gln | Ser | Leu | Ala | Asn | Leu | Gln | Ser | Gly |
|     |     |     | 900 |     |     |     |     | 905 |     |     |     |     | 910 |     |     |
| Arg | Asp | Val | Lys | Asp | Leu | Leu | Met | Leu | Cys | Trp | Thr | Tyr | Glu | Lys | Glu |
|     |     | 915 |     |     |     |     | 920 |     |     |     |     | 925 |     |     |     |
| His | Arg | Pro | Gln | Phe | Ala | Arg | Leu | Leu | Ser | Leu | Leu | Glu | His | Leu | Pro |
| 930 |     |     |     |     | 935 |     |     |     |     | 940 |     |     |     |     |     |

| Lys | Lys | Arg | Leu | Ala | Arg | Ser | Pro | Ser | His | Pro | Val | Asn | Leu | Ser | Arg |
| | | | | 950 | | | | | 955 | | | | | | 960 |
945

Ser Ala Glu Ser Val Phe
                    965

( 2 ) INFORMATION FOR SEQ ID NO:3:

( i ) SEQUENCE CHARACTERISTICS:
        ( A ) LENGTH: 3681 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
CCCCCAAAAA CTATAAATT  TTTCGCGTTT TTCTCATAGC AGAAGCTGTC TCGAAGTCCG     60
CATTTCGCAG GACTGTTCAT GTGTGCTTGC AGCAAGCGAA AAAAGCTGGT TGATGTGGAC    120
AGAATGTGTG TCAAAGTGGT GCAAACAACA AATGATTTGT AAGTGCGTCT GAAAAAATCA    180
ATCAGTTTGT ACTGCTGGAA GGGGCGGGCG GGCCACAACA AATGAGCAG  CAGCGCCGCC    240
GCCCAGCTGA CTGCGCCGCC AGTCAGCAAC AGCAACAGCA GCAGCAGTAA CAACAATACA    300
ACAACGACTG CGAGCGAAAG CAATCTAATC ATCATACAGG ATATGATTGA TCTCTCGGCC    360
AACCATCTGG AGGGTCTGCG AACACAGTGC GCAACGAGCG CGACGTTGAC GCAACAGGAG    420
ATCCGCTGCC TAGAGTCCAA GTTGGTGCGC TACTTCTCCG AACTGCTCTT GACCAAAACG    480
AGACTCAACG AACGCATACC CGCGAACGGT CTGCTGCCCC ATCATCAGGC TACCGGGAAC    540
GAGTTGCGCC AATGGCTGCG AGTAGTTGGA CTCAGTCCGG AGTCACTGAA TGCATGCCTA    600
GCGCGTCTAA CGACATTGGA GCAAACACTG CAGCTGAGCG ATGAAGAACT GAAACAACTG    660
CTTGCCCACA ATTCAAGTAC CCAGCTGGAC GAGGAACTGC GGCGGCTGAC CAAAGCGATG    720
CATAATCTCC GAAAATGCAT GGAAACGCTG GACAGCAGCG CGCAGTTGC  GTCCAACGTC    780
GATCCGGAAC AATGGCACTG GGACTCCTGG GATCGACCCC ATCCGCATCA CATGCACCGC    840
GGCAGCATTG GCAATATTGG CCTAGGACTA AGCAGCGCCT CACCTCGCGC CCATCATCGT    900
CAACATCAAC ATCAACACGC GAACAGCAAG CCGAAAATTG TTAACAATTC TGCCTCAAGC    960
TCCGCAGCG  AACAGCAACC ACTGACTGGT TCTCAGTTGA CCTTAACACT GACGCCCTCG   1020
CCACCCAACT CGCCCTTTAC GCCCGCCTCA GGGACGGCAT CCGCCAGCGG CACTCCGCAG   1080
CGCAGCCGCA GTACCACAAC AGCGGCGGGA ACGCCACCAC CAGCCAAGAA GCATCAAACG   1140
CTGCTCATGC ACAACAGCAG CGCTTCGGAA ACGGCACTCG GGAGCAGCC  TCCACGGCCA   1200
CCGCGCAGCC GTCTACCCAC AGATCCTAGC CCGGATAGCC ACAGCTCGGC CAGCAGTTCG   1260
GACATTTTTG TGGACGGTGG CAGTATCAAC AGCTCCAATG TACTACTAGT GCCGCCCTCG   1320
CCAGGTGTGG CACACGTGGG CATGGGTCAT ACCATTAAGC ACCGTTTCAG TAAATGGTTT   1380
GGCTTCATGG CCACGTGCAA ACTGTGCCAA AAGCAGATGA TGAGCCACTG GTTCAAGTGC   1440
ACCGACTGCA AATATATTTG CCACAAGTCC TGTGCGCCGC ATGTGCCGCC CTCGTGTGGC   1500
CTTCCACCCG AATATGTTCA CGAGTTTCGT CAAACTCAGG TGGGCGGCAG ATGGGACCCT   1560
GCGCAGCACA GCAGCAGCAA GGCATCACCA GTGCCCAGGA AGAGCACGCT GGGCAAACCG   1620
CAATTGCAGC AGCCACAGCT GCAGCACGGG GACAGCAGCT CACCAAGCTC GAGCTGCACC   1680
AGCTCAACGC CCAGCAGTCC AGCATTGTTC CAGCAGCAGC AACTGCAACT GGCCACGCCC   1740
AGCGCCTGCC AGCCGAAACC AGCACCAGCA GCGGTAGCAG CAGCAGCAAC ACAACAGGGT   1800
CAACAGAGTC AATTCAATTT CCCCAACGTG ACCATCACAA GCATCAATGC CTGCAATAGT   1860
```

| | | | | |
|---|---|---|---|---|
| AACGCCAGCG | CTGCCCAAAC | GCTCATATCC | AATGAGCCGC | AAGCGCATAT GGCCACAACG | 1920 |
| GAGTCCACGC | TGACCAATGG | CAACAACAAC | AGCAGCTCCA | ACAACGGGAG CAGCGCCAAC | 1980 |
| AACAATAGCA | GCAGCAGCAG | CAGCTGCTCC | AATGGTCACC | TGCACTCGCT GACTGGAAGT | 2040 |
| CAAGTGTCCA | CGCATTCGGC | TACCTCGCAA | GTGTCGAATG | TCAGTGGCAG CAGCTCGGCC | 2100 |
| ACCTACACCT | CCAGTCTGGT | GAACAGCGGC | AGTTTCTTTC | CGCGGAAATT GAGCAATGCT | 2160 |
| GGCGTGGACA | AGCGGGTGCC | CTTTACCAGC | GAATATACGG | ACACGCACAA GTCGAATGAT | 2220 |
| AGCGACAAGA | CGGTTTCGTT | GTCGGGCAGC | GCCAGCACTG | ACTCGGATCG CACGCCTGTG | 2280 |
| CGTTTGGACT | CCACAGAGGA | TGGCGACTCG | GGCCAATGGC | GGCAGAACTC CATATCATTG | 2340 |
| AAGGAATGGG | ATATACCCTA | TGGCGATTTG | CACTTGCTGG | AGCGCATTGG ACAGGGTCGA | 2400 |
| TTTGGCACCG | TGCATCGGGC | ACTGTGGCAT | GGCGATGTCG | CTGTGAAGCT GCTCAATGAA | 2460 |
| GACTATCTGC | AGGACGAGCA | CATGCTGGAA | TCGTTTCGCA | ACGAGGTGGC CAATTTCAAG | 2520 |
| AAGACGCGAC | ACGAGAATCT | GGTGCTGTTC | ATGGGCGCCT | GCATGAATCC GCCGTATTTG | 2580 |
| GCCATTGTCA | CGGCACTATG | CAAGGGCAAC | ACCCTGTACA | CCTATATACA TCAGCGAAGG | 2640 |
| GAGAAGTTTG | CAATGAATCG | CACGTTGTTG | ATTGCCCAAC | AGATTGCCCA GGGCATGGGC | 2700 |
| TATTTGCATG | CCAGGGACAT | AATACACAAG | GATCTGCGCA | CCAAGAACAT TTTTATAGAG | 2760 |
| AATGGCAAGG | TGATCATTAC | GGACTTTGGC | CTATTCAGCT | CCACAAAGCT GCTGTACTGT | 2820 |
| GATATGGGCT | GGGTGTTCC | ACAAAACTGG | CTCTGCTACC | TGGCCCCGGA ACTAATACGC | 2880 |
| GCCCTGCAGC | CGTGCAAGCC | ACCCGGCGAG | TGTCTAGAGT | TCACGTCCTA CTCGGATGTT | 2940 |
| TACTCATTTG | GCACCGTTTG | GTACGAGCTA | ATTTGCGGCG | AATTCACGTT CAAGGATCAA | 3000 |
| CCGGCGGAGT | CAATCATTTG | GCAAGTGGGG | CGCGGCATGA | AACAGTCGCT GGCCAATCTG | 3060 |
| CAGTCTGGTC | GTGATGTCAA | GGACCTGCTG | ATGCTGTGCT | GGACCTATGA AAAGGAGCAC | 3120 |
| AGGCCGGACT | TTGCACGTCT | GCTCTCCTTG | CTGGAGCATT | TGCCAAAGAA GCGCCTGGCA | 3180 |
| CGCAGTCCCT | CGCATCCTGT | CAACCTCTCG | CGCTCAGCGG | AATCTGTATT CTAACCAGCC | 3240 |
| GATATACAAA | TATATACGTT | TATAGACAAA | TATGTCATAT | ATGTAAGCAG GCGCGCACAC | 3300 |
| ACTCACACAC | ACACACACTC | TATTTAGCAC | AATTTCACGT | TATATGTAAA TGTAAGCTAC | 3360 |
| ACACATATGC | AAACATACGT | ATGTCACTTT | AACTGTAATT | GTTGTGCGTG CAAAATGTCA | 3420 |
| AATGTGAAAT | TAGCTCTCCG | GTAAGGGAAG | CAAGAGAATG | CGGAGAGCAA AGCTCACTTC | 3480 |
| CTCAGCCTCA | TGTATGTGTA | TGTATGTGTA | CGACCCTACG | ACTCTCAAAG AAAAGTTCAA | 3540 |
| AGTGCATGTG | TTACAAAACA | AAAAACTGTA | AATATACATT | TAAAGCAAAT GAAACGAAAC | 3600 |
| TATACATATA | TGTGTATATC | CAATTATAGC | AATTTACAAA | TGCATTGTCA AAATAGTTTT | 3660 |
| TATCTTTAAT | TATGTATTGA | A | | | 3681 |

( 2 ) INFORMATION FOR SEQ ID NO:4:

( i ) SEQUENCE CHARACTERISTICS:
        ( A ) LENGTH: 1003 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:4:

```
Met  Ser  Ser  Ser  Ala  Ala  Ala  Gln  Leu  Thr  Ala  Pro  Pro  Val  Ser  Asn
 1                  5                    10                       15

Ser  Asn  Ser  Ser  Ser  Ser  Asn  Asn  Asn  Thr  Thr  Thr  Thr  Ala  Ser  Glu
```

-continued

```
                          20                        25                          30
        Ser  Asn  Leu  Ile  Ile  Ile  Gln  Asp  Met  Ile  Asp  Leu  Ser  Ala  Asn  His
                  35                       40                   45
        Leu  Glu  Gly  Leu  Arg  Thr  Gln  Cys  Ala  Thr  Ser  Ala  Thr  Leu  Thr  Gln
             50                       55                       60
        Gln  Glu  Ile  Arg  Cys  Leu  Glu  Ser  Lys  Leu  Val  Arg  Tyr  Phe  Ser  Glu
        65                       70                       75                        80
        Leu  Leu  Leu  Thr  Lys  Thr  Arg  Leu  Asn  Glu  Arg  Ile  Pro  Ala  Asn  Gly
                            85                       90                   95
        Leu  Leu  Pro  His  His  Gln  Ala  Thr  Gly  Asn  Glu  Leu  Arg  Gln  Trp  Leu
                       100                      105                 110
        Arg  Val  Val  Gly  Leu  Ser  Pro  Glu  Ser  Leu  Asn  Ala  Cys  Leu  Ala  Arg
                  115                      120                      125
        Leu  Thr  Thr  Leu  Glu  Gln  Thr  Leu  Gln  Leu  Ser  Asp  Glu  Glu  Leu  Lys
             130                      135                      140
        Gln  Leu  Leu  Ala  His  Asn  Ser  Ser  Thr  Gln  Leu  Asp  Glu  Glu  Leu  Arg
        145                      150                      155                      160
        Arg  Leu  Thr  Lys  Ala  Met  His  Asn  Leu  Arg  Lys  Cys  Met  Glu  Thr  Leu
                            165                      170                      175
        Asp  Ser  Ser  Gly  Ala  Val  Ala  Ser  Asn  Val  Asp  Pro  Glu  Gln  Trp  His
                       180                      185                 190
        Trp  Asp  Ser  Trp  Asp  Arg  Pro  His  Pro  His  Met  His  Arg  Gly  Ser
                  195                      200                      205
        Ile  Gly  Asn  Ile  Gly  Leu  Gly  Leu  Ser  Ser  Ala  Ser  Pro  Arg  Ala  His
             210                      215                      220
        His  Arg  Gln  His  Gln  His  Gln  His  Ala  Asn  Ser  Lys  Pro  Lys  Ile  Val
        225                      230                      235                      240
        Asn  Asn  Ser  Ala  Ser  Ser  Ser  Arg  Ser  Glu  Gln  Gln  Pro  Leu  Thr  Gly
                            245                      250                      255
        Ser  Gln  Leu  Thr  Leu  Thr  Leu  Thr  Pro  Ser  Pro  Pro  Asn  Ser  Pro  Phe
                       260                      265                 270
        Thr  Pro  Ala  Ser  Gly  Thr  Ala  Ser  Ala  Ser  Gly  Thr  Pro  Gln  Arg  Ser
                  275                      280                      285
        Arg  Ser  Thr  Thr  Thr  Ala  Ala  Gly  Thr  Pro  Pro  Ala  Lys  Lys  His
             290                      295                      300
        Gln  Thr  Leu  Leu  Met  His  Asn  Ser  Ser  Ala  Ser  Glu  Thr  Ala  Leu  Ala
        305                      310                      315                      320
        Glu  Gln  Pro  Pro  Arg  Pro  Pro  Arg  Ser  Arg  Leu  Pro  Thr  Asp  Pro  Ser
                            325                      330                      335
        Pro  Asp  Ser  His  Ser  Ser  Ala  Ser  Ser  Ser  Asp  Ile  Phe  Val  Asp  Gly
                       340                      345                 350
        Gly  Ser  Ile  Asn  Ser  Ser  Asn  Val  Leu  Leu  Val  Pro  Pro  Ser  Pro  Gly
                  355                      360                      365
        Val  Ala  His  Val  Gly  Met  Gly  His  Thr  Ile  Lys  His  Arg  Phe  Ser  Lys
             370                      375                      380
        Trp  Phe  Gly  Phe  Met  Ala  Thr  Cys  Lys  Leu  Cys  Gln  Lys  Gln  Met  Met
        385                      390                      395                      400
        Ser  His  Trp  Phe  Lys  Cys  Thr  Asp  Cys  Lys  Tyr  Ile  Cys  His  Lys  Ser
                            405                      410                      415
        Cys  Ala  Pro  His  Val  Pro  Pro  Ser  Cys  Gly  Leu  Pro  Pro  Glu  Tyr  Val
                       420                      425                 430
        His  Glu  Phe  Arg  Gln  Thr  Gln  Val  Gly  Gly  Arg  Trp  Asp  Pro  Ala  Gln
                  435                      440                      445
```

| | | | | | | | | | | | | | |
|---|---|---|---|---|---|---|---|---|---|---|---|---|---|
|His|Ser|Ser|Ser|Lys|Ala|Ser|Pro|Val|Pro|Arg|Lys|Ser|Thr|Leu|Gly|
| |450| | | |455| | | |460| | | | |
|Lys|Pro|Gln|Leu|Gln|Gln|Pro|Gln|Leu|Gln|His|Gly|Asp|Ser|Ser|Ser|
|465| | | | |470| | | |475| | | | |480|
|Pro|Ser|Ser|Ser|Cys|Thr|Ser|Ser|Thr|Pro|Ser|Ser|Pro|Ala|Leu|Phe|
| | | | |485| | | |490| | | | |495|
|Gln|Gln|Gln|Gln|Leu|Gln|Leu|Ala|Thr|Pro|Ser|Ala|Cys|Gln|Pro|Lys|
| | | |500| | | |505| | | | |510|
|Pro|Ala|Pro|Ala|Ala|Val|Ala|Ala|Ala|Thr|Gln|Gln|Gly|Gln|Gln|
| | |515| | | |520| | | |525|
|Ser|Gln|Phe|Asn|Phe|Pro|Asn|Val|Thr|Ile|Thr|Ser|Ile|Asn|Ala|Cys|
| |530| | | |535| | | |540|
|Asn|Ser|Asn|Ala|Ser|Ala|Ala|Gln|Thr|Leu|Ile|Ser|Asn|Glu|Pro|Gln|
|545| | | |550| | | |555| | | |560|
|Ala|His|Met|Ala|Thr|Thr|Glu|Ser|Thr|Leu|Thr|Asn|Gly|Asn|Asn|Asn|
| | | |565| | | |570| | | |575|
|Ser|Ser|Ser|Asn|Asn|Gly|Ser|Ser|Ala|Asn|Asn|Ser|Ser|Ser|Ser|
| | |580| | | |585| | | |590|
|Ser|Ser|Cys|Ser|Asn|Gly|His|Leu|His|Ser|Leu|Thr|Gly|Ser|Gln|Val|
| |595| | | |600| | | |605|
|Ser|Thr|His|Ser|Ala|Thr|Ser|Gln|Val|Ser|Asn|Val|Ser|Gly|Ser|Ser|
|610| | | |615| | | |620|
|Ser|Ala|Thr|Tyr|Thr|Ser|Ser|Leu|Val|Asn|Ser|Gly|Ser|Phe|Phe|Pro|
|625| | | |630| | | |635| | | |640|
|Arg|Lys|Leu|Ser|Asn|Ala|Gly|Val|Asp|Lys|Arg|Val|Pro|Phe|Thr|Ser|
| | | |645| | | |650| | | |655|
|Glu|Tyr|Thr|Asp|Thr|His|Lys|Ser|Asn|Asp|Ser|Asp|Lys|Thr|Val|Ser|
| | |660| | | |665| | | |670|
|Leu|Ser|Gly|Ser|Ala|Ser|Thr|Asp|Ser|Asp|Arg|Thr|Pro|Val|Arg|Leu|
| |675| | | |680| | | |685|
|Asp|Ser|Thr|Glu|Asp|Gly|Asp|Ser|Gly|Gln|Trp|Arg|Gln|Asn|Ser|Ile|
|690| | | |695| | | |700|
|Ser|Leu|Lys|Glu|Trp|Asp|Ile|Pro|Tyr|Gly|Asp|Leu|His|Leu|Leu|Glu|
|705| | | |710| | | |715| | | |720|
|Arg|Ile|Gly|Gln|Gly|Arg|Phe|Gly|Thr|Val|His|Arg|Ala|Leu|Trp|His|
| | | |725| | | |730| | | |735|
|Gly|Asp|Val|Ala|Val|Lys|Leu|Leu|Asn|Glu|Asp|Tyr|Leu|Gln|Asp|Glu|
| | |740| | | |745| | | |750|
|His|Met|Leu|Glu|Ser|Phe|Arg|Asn|Glu|Val|Ala|Asn|Phe|Lys|Lys|Thr|
| |755| | | |760| | | |765|
|Arg|His|Glu|Asn|Leu|Val|Leu|Phe|Met|Gly|Ala|Cys|Met|Asn|Pro|Pro|
|770| | | |775| | | |780|
|Tyr|Leu|Ala|Ile|Val|Thr|Ala|Leu|Cys|Lys|Gly|Asn|Thr|Leu|Tyr|Thr|
|785| | | |790| | | |795| | | |800|
|Tyr|Ile|His|Gln|Arg|Arg|Glu|Lys|Phe|Ala|Met|Asn|Arg|Thr|Leu|Leu|
| | | |805| | | |810| | | |815|
|Ile|Ala|Gln|Gln|Ile|Ala|Gln|Gly|Met|Gly|Tyr|Leu|His|Ala|Arg|Asp|
| | | |820| | | |825| | | |830|
|Ile|Ile|His|Lys|Asp|Leu|Arg|Thr|Lys|Asn|Ile|Phe|Ile|Glu|Asn|Gly|
| | |835| | | |840| | | |845|
|Lys|Val|Ile|Ile|Thr|Asp|Phe|Gly|Leu|Phe|Ser|Ser|Thr|Lys|Leu|Leu|
|850| | | |855| | | |860|
|Tyr|Cys|Asp|Met|Gly|Leu|Gly|Val|Pro|Gln|Asn|Trp|Leu|Cys|Tyr|Leu|
|865| | | |870| | | |875| | | |880|

| | | | | | | | | | | | | | |
|---|---|---|---|---|---|---|---|---|---|---|---|---|---|
| Ala | Pro | Glu | Leu | Ile<br>885 | Arg | Ala | Leu | Gln | Pro<br>890 | Cys | Lys | Pro | Pro | Gly<br>895 | Glu |
| Cys | Leu | Glu | Phe<br>900 | Thr | Ser | Tyr | Ser | Asp<br>905 | Val | Tyr | Ser | Phe | Gly<br>910 | Thr | Val |
| Trp | Tyr | Glu<br>915 | Leu | Ile | Cys | Gly | Glu<br>920 | Phe | Thr | Phe | Lys | Asp<br>925 | Gln | Pro | Ala |
| Glu | Ser<br>930 | Ile | Ile | Trp | Gln | Val<br>935 | Gly | Arg | Gly | Met | Lys<br>940 | Gln | Ser | Leu | Ala |
| Asn<br>945 | Leu | Gln | Ser | Gly | Arg<br>950 | Asp | Val | Lys | Asp | Leu<br>955 | Leu | Met | Leu | Cys | Trp<br>960 |
| Thr | Tyr | Glu | Lys | Glu<br>965 | His | Arg | Pro | Asp | Phe<br>970 | Ala | Arg | Leu | Leu | Ser<br>975 | Leu |
| Leu | Glu | His | Leu<br>980 | Pro | Lys | Lys | Arg | Leu<br>985 | Ala | Arg | Ser | Pro | Ser<br>990 | His | Pro |
| Val | Asn | Leu<br>995 | Ser | Arg | Ser | Ala | Glu<br>1000 | Ser | Val | Phe | | | | | |

( 2 ) INFORMATION FOR SEQ ID NO:5:

( i ) SEQUENCE CHARACTERISTICS:
      ( A ) LENGTH: 4094 base pairs
      ( B ) TYPE: nucleic acid
      ( C ) STRANDEDNESS: double
      ( D ) TOPOLOGY: linear ( i i ) MOLECULE TYPE: cDNA ( x i ) SEQUENCE DESCRIPTION: SEQ ID NO:5:

| | | | | | |
|---|---|---|---|---|---|
| GAATTCCCTC | GGGGCTTTCC | TGCCGAGGCG | CCCGTGTCCC | CGGGCTCCTC | GCCTCGGCCC | 60 |
| CCAGCGGCCC | CGATGCCGAG | GCATGGATAG | AGCGGCGTTG | CGCGCGGCAG | CGATGGGCGA | 120 |
| GAAAAAGGAG | GGCGGCGGCG | GGGGCGCCGC | GGCGGACGGG | GGCGCAGGGG | CCGCCGTCAG | 180 |
| CCGGGCGCTG | CAGCAGTGCG | GCCAGCTGCA | GAAGCTCATC | GATATCTCCA | TCGGCAGTCT | 240 |
| GCGCGGGCTG | CGCACCAAGT | GCTCAGTGTC | TAACGACCTC | ACACAGCAGG | AGATCCGGAC | 300 |
| CCTAGAGGCA | AAGCTGGTGA | AATACATTTG | CAAGCAGCAG | CAGAGCAAGC | TTAGTGTGAC | 360 |
| CCCAAGCGAC | AGGACCGCCG | AGCTCAACAG | CTACCCACGC | TTCAGTGACT | GGCTGTACAT | 420 |
| CTTCAACGTG | AGGCCTGAGG | TGGTGCAGGA | GATCCCCCAA | GAGCTCACAC | TGGATGCTCT | 480 |
| GCTGGAGATG | GACGAGGCCA | AAGCCAAGGA | GATGCTGCGG | CGCTGGGGGG | CCAGCACGGA | 540 |
| GGAGTGCAGC | CGCCTACAGC | AAGCCCTTAC | CTGCCTTCGG | AAGGTGACTG | GCCTGGGAGG | 600 |
| GGAGCACAAA | ATGGACTCAG | GTTGGAGTTC | AACAGATGCT | CGAGACAGTA | GCTTGGGGCC | 660 |
| TCCCATGGAC | ATGCTTTCCT | CGCTGGGCAG | AGCGGGTGCC | AGCACTCAGG | GACCCCGTTC | 720 |
| CATCTCCGTG | TCCGCCCTGC | CTGCCTCAGA | CTCTCCGGTC | CCCGGCCTCA | GTGAGGGCCT | 780 |
| CTCGGACTCC | TGTATCCCCT | TGCACACCAG | CGGCCGGCTG | ACCCCCGGG | CCCTGCACAG | 840 |
| CTTCATCACG | CCCCCTACCA | CACCCCAGCT | ACGACGGCAC | GCCAAGCTGA | AGCCACCAAG | 900 |
| GACACCCCCA | CCGCCAAGCC | GCAAGGTCTT | CCAGCTGCTC | CCCAGCTTCC | CCACACTCAC | 960 |
| ACGGAGCAAG | TCCCACGAGT | CCCAGCTGGG | AAACCGAATC | GACGACGTCA | CCCCGATGAA | 1020 |
| GTTTGAACTC | CCTCATGGAT | CCCCACAGCT | GGTACGAAGG | GATATCGGGC | TCTCGGTGAC | 1080 |
| GCACAGGTTC | TCCACAAAGT | CATGGTTGTC | ACAGGTGTGC | AACGTGTGCC | AGAAGAGCAT | 1140 |
| GATTTTTGGC | GTGAAGTGCA | AACACTGCAG | GTTAAAATGC | CATAACAAGT | GCACAAAGGA | 1200 |
| AGCTCCCGCC | TGCAGGATCA | CCTTCCTCCC | ACTGGCCAGG | CTTCGGAGGA | CAGAGTCTGT | 1260 |

| | | | | | |
|---|---|---|---|---|---|
| CCCGTCAGAT | ATCAACAACC | CAGTGGACAG | AGCAGCAGAG | CCCCATTTTG | GAACCCTTCC | 1320 |
| CAAGGCCCTG | ACAAAGAAGG | AGCACCCTCC | AGCCATGAAC | CTGGACTCCA | GCAGCAACCC | 1380 |
| ATCCTCCACC | ACGTCCTCCA | CACCCTCATC | GCCGGCACCT | TTCCTGACCT | CATCTAATCC | 1440 |
| CTCCAGTGCC | ACCACGCCTC | CCAACCCGTC | ACCTGGCCAG | CGGGACAGCA | GGTTCAGCTT | 1500 |
| CCCAGACATT | TCAGCCTGTT | CTCAGGCAGC | CCCGCTGTCC | AGCACAGCCG | ACAGTACACG | 1560 |
| GCTCGACGAC | CAGCCCAAAA | CAGATGTGCT | AGGTGTTCAC | GAAGCAGAGG | CTGAGGAGCC | 1620 |
| TGAGGCTGGC | AAGTCAGAGG | CAGAGGATGA | CGAGGAGGAT | GAGGTGGACG | ACCTCCCCAG | 1680 |
| CTCCCGCCGG | CCCTGGAGGG | GCCCCATCTC | TCGAAAGGCC | AGCCAGACCA | GCGTTTACCT | 1740 |
| GCAAGAGTGG | GACATCCCCT | TTGAACAGGT | GGAACTGGGC | GAGCCCATTG | ACAGGGTCG | 1800 |
| CTGGGGCCGG | GTGCACCGAG | GCCGTTGGCA | TGGCGAGGTG | GCCATTCGGC | TGCTGGAGAT | 1860 |
| GGACGGCCAC | AATCAGGACC | ACCTGAAGCT | GTTCAAGAAA | GAGGTGATGA | ACTACCGGCA | 1920 |
| GACGCGGCAT | GAGAACGTGG | TGCTCTTCAT | GGGGGCCTGC | ATGAACCCAC | CTCACCTGGC | 1980 |
| CATTATCACC | AGCTTCTGCA | AGGGGCGGAC | ATTGCATTCA | TTCGTGAGGG | ACCCCAAGAC | 2040 |
| GTCTCTGGAC | ATCAATAAGA | CTAGGCAGAT | CGCCCAGGAG | ATCATCAAGG | GCATGGGTTA | 2100 |
| TCTTCATGCA | AAAGGCATCG | TGCACAAGGA | CCTCAAGTCC | AAGAATGTCT | TCTATGACAA | 2160 |
| CGGCAAAGTG | GTCATCACAG | ACTTCGGGCT | GTTTGGGATC | TCGGGTGTGG | TCCGAGAGGA | 2220 |
| ACGGCGCGAG | AACCAACTGA | AACTGTCACA | TGACTGGCTG | TGCTACCTGG | CCCCCGAGAT | 2280 |
| CGTACGAGAA | ATGATCCCGG | GGCGGGACGA | GGACCAGCTG | CCCTTCTCCA | AAGCAGCCGA | 2340 |
| TGTCTATGCA | TTCGGGACTG | TGTGGTATGA | ACTACAGGCA | AGAGACTGGC | CCTTTAAGCA | 2400 |
| CCAGCCTGCT | GAGGCCTTGA | TCTGGCAGAT | TGGAAGTGGG | GAAGGAGTAC | GGCGCGTCCT | 2460 |
| GGCATCCGTC | AGCCTGGGGA | AGGAAGTCGG | CGAGATCCTG | TCTGCCTGCT | GGGCTTTCGA | 2520 |
| TCTGCAGGAG | AGACCCAGCT | TCAGCCTGCT | GATGGACATG | CTGGAGAGGC | TGCCCAAGCT | 2580 |
| GAACCGGCGG | CTCTCCCACC | CTGGGCACTT | TTGGAAGTCG | GCTGACATTA | ACAGCAGCAA | 2640 |
| AGTCATGCCC | CGCTTTGAAA | GGTTTGGCCT | GGGGACCCTG | GAGTCCGGTA | ATCCAAAGAT | 2700 |
| GTAGCCAGCC | CTGCACGTTC | ATGCAGAGAG | TGTCTTCCTT | TCGAAAACAT | GATCACGAAA | 2760 |
| CATGCAGACC | ACCACCTCAA | GGAATCAGAA | GCATTGCATC | CCAAGCTGCG | GACTGGGAGC | 2820 |
| GTGTCTCCTC | CCTAAAGGAC | GTGCGTGCGT | GCGTGCGTGC | GTGCGTGCGT | GCGTGCGTCA | 2880 |
| CCAAGGTGTG | TGGAGCTCAG | GATCGCAGCC | ATACACGCAA | CTCCAGATGA | TACCACTACC | 2940 |
| GCCAGTGTTT | ACACAGAGGT | TTCTGCCTGG | CAAGCTTGGT | ATTTTACAGT | AGGTGAAGAT | 3000 |
| CATTCTGCAG | AAGGGTGCTG | GCACAGTGGA | GCAGCACGGA | TGTCCCCAGC | CCCCGTTCTG | 3060 |
| GAAGACCCTA | CAGCTGTGAG | AGGCCCAGGG | TTGAGCCAGA | TGAAAGAAAA | GCTGCGTGGG | 3120 |
| TGTGGGCTGT | ACCCGGAAAA | GGGCAGGTGG | CAGGAGGTTT | GCCTTGGCCT | GTGCTTGGGC | 3180 |
| CGAGAACCAC | ACTAAGGAGC | AGCAGCCTGA | GTTAGGAATC | TATCTGGATT | ACGGGGATCA | 3240 |
| GAGTTCCTGG | AGAGTGGACT | CAGTTTCTGC | TCTGATCCAG | GCCTGTTGTG | CTTTTTTTT | 3300 |
| TTCCCCCTTA | AAAAAAAAA | AGTACAGACA | GAATCTCAGC | GGCTTCTAGA | CTGATCTGAT | 3360 |
| GGATCTTAGC | CCGGCTTCTA | CTGCGGGGGG | GAGGGGGGA | GGGATAGCCA | CATATCTGTG | 3420 |
| GAGACACCCA | CTTCTTTATC | TGAGGCCTCC | AGGTAGGCAC | AAAGGCTGTG | GAACTCAGCC | 3480 |
| TCTATCATCA | GACACCCCCC | CCCAATGCCT | CATTGACCCC | CTTCCCCCAG | AGCCAAGGGC | 3540 |
| TAGCCCATCG | GGTGTGTGTA | CAGTAAGTTC | TTGGTGAAGG | AGAACAGGGA | CGTTGGCAGA | 3600 |
| AGCAGTTTGC | AGTGGCCCTA | GCATCTTAAA | ACCCATTGTC | TGTCACACCA | GAAGGTTCTA | 3660 |

```
GACCTACCAC CACTTCCCTT CCCCATCTCA TGGAAACCTT TTAGCCCATT CTGACCCCTG    3720

TGTGTGCTCT GAGCTCAGAT CGGGTTATGA GACCGCCCAG GCACATCAGT CAGGGAGGCT    3780

CTGATGTGAG CCGCAGACCT CTGTGTTCAT TCCTATGAGC TGGAGGGGCT GGACTGGGTG    3840

GGGTCAGATG TGCTTGGCAG GAACTGTCAG CTGCTGAGCA GGGTGGTCCC TGAGCGGAGG    3900

ATAAGCAGCA TCAGACTCCA CAACCAGAGG AAGAAAGAAA TGGGGATGGA GCGGAGACCC    3960

ACGGGCTGAG TCCCGCTGTG GAGTGGCCTT GCAGCTCCCT CTCAGTTAAA ACTCCCAGTA    4020

AAGCCACAGT TCTCCGAGCA CCCAAGTCTG CTCCAGCCGT CTCTTAAAAC AGGCCACTCT    4080

CTGAGAAGGA ATTC                                                    4094
```

( 2 ) INFORMATION FOR SEQ ID NO:6:

( i ) SEQUENCE CHARACTERISTICS:
        ( A ) LENGTH: 873 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:6:

```
Met Asp Arg Ala Ala Leu Arg Ala Ala Ala Met Gly Glu Lys Lys Glu
 1               5                  10                  15

Gly Gly Gly Gly Gly Ala Ala Ala Asp Gly Gly Ala Gly Ala Ala Val
            20                  25                  30

Ser Arg Ala Leu Gln Gln Cys Gly Gln Leu Gln Lys Leu Ile Asp Ile
        35                  40                  45

Ser Ile Gly Ser Leu Arg Gly Leu Arg Thr Lys Cys Ser Val Ser Asn
 50                  55                  60

Asp Leu Thr Gln Gln Glu Ile Arg Thr Leu Glu Ala Lys Leu Val Lys
65                  70                  75                  80

Tyr Ile Cys Lys Gln Gln Gln Ser Lys Leu Ser Val Thr Pro Ser Asp
                85                  90                  95

Arg Thr Ala Glu Leu Asn Ser Tyr Pro Arg Phe Ser Asp Trp Leu Tyr
            100                 105                 110

Ile Phe Asn Val Arg Pro Glu Val Val Gln Glu Ile Pro Gln Glu Leu
        115                 120                 125

Thr Leu Asp Ala Leu Leu Glu Met Asp Glu Ala Lys Ala Lys Glu Met
    130                 135                 140

Leu Arg Arg Trp Gly Ala Ser Thr Glu Glu Cys Ser Arg Leu Gln Gln
145                 150                 155                 160

Ala Leu Thr Cys Leu Arg Lys Val Thr Gly Leu Gly Gly Glu His Lys
                165                 170                 175

Met Asp Ser Gly Trp Ser Ser Thr Asp Ala Arg Asp Ser Ser Leu Gly
            180                 185                 190

Pro Pro Met Asp Met Leu Ser Ser Leu Gly Arg Ala Gly Ala Ser Thr
        195                 200                 205

Gln Gly Pro Arg Ser Ile Ser Val Ser Ala Leu Pro Ala Ser Asp Ser
    210                 215                 220

Pro Val Pro Gly Leu Ser Glu Gly Leu Ser Asp Ser Cys Ile Pro Leu
225                 230                 235                 240

His Thr Ser Gly Arg Leu Thr Pro Arg Ala Leu His Ser Phe Ile Thr
                245                 250                 255

Pro Pro Thr Thr Pro Gln Leu Arg Arg His Ala Lys Leu Lys Pro Pro
            260                 265                 270
```

```
Arg Thr Pro Pro Pro Pro Ser Arg Lys Val Phe Gln Leu Leu Pro Ser
    275             280                 285

Phe Pro Thr Leu Thr Arg Ser Lys Ser His Glu Ser Gln Leu Gly Asn
    290             295                 300

Arg Ile Asp Asp Val Thr Pro Met Lys Phe Glu Leu Pro His Gly Ser
305             310                 315                     320

Pro Gln Leu Val Arg Arg Asp Ile Gly Leu Ser Val Thr His Arg Phe
                325             330                 335

Ser Thr Lys Ser Trp Leu Ser Gln Val Cys Asn Val Cys Gln Lys Ser
            340             345                 350

Met Ile Phe Gly Val Lys Cys Lys His Cys Arg Leu Lys Cys His Asn
            355             360                 365

Lys Cys Thr Lys Glu Ala Pro Ala Cys Arg Ile Thr Phe Leu Pro Leu
    370                 375                 380

Ala Arg Leu Arg Arg Thr Glu Ser Val Pro Ser Asp Ile Asn Asn Pro
385             390                 395                     400

Val Asp Arg Ala Ala Glu Pro His Phe Gly Thr Leu Pro Lys Ala Leu
                405             410                 415

Thr Lys Lys Glu His Pro Pro Ala Met Asn Leu Asp Ser Ser Ser Asn
            420             425                 430

Pro Ser Ser Thr Thr Ser Ser Thr Pro Ser Ser Pro Ala Pro Phe Leu
        435             440                 445

Thr Ser Ser Asn Pro Ser Ser Ala Thr Thr Pro Pro Asn Pro Ser Pro
    450             455                 460

Gly Gln Arg Asp Ser Arg Phe Ser Phe Pro Asp Ile Ser Ala Cys Ser
465             470                 475                     480

Gln Ala Ala Pro Leu Ser Ser Thr Ala Asp Ser Thr Arg Leu Asp Asp
                485             490                 495

Gln Pro Lys Thr Asp Val Leu Gly Val His Glu Ala Glu Ala Glu Glu
            500             505                 510

Pro Glu Ala Gly Lys Ser Glu Ala Glu Asp Asp Glu Glu Asp Glu Val
        515             520                 525

Asp Asp Leu Pro Ser Ser Arg Arg Pro Trp Arg Gly Pro Ile Ser Arg
    530             535                 540

Lys Ala Ser Gln Thr Ser Val Tyr Leu Gln Glu Trp Asp Ile Pro Phe
545             550                 555                     560

Glu Gln Val Glu Leu Gly Glu Pro Ile Gly Gln Gly Arg Trp Gly Arg
                565             570                 575

Val His Arg Gly Arg Trp His Gly Glu Val Ala Ile Arg Leu Leu Glu
            580             585                 590

Met Asp Gly His Asn Gln Asp His Leu Lys Leu Phe Lys Lys Glu Val
        595             600                 605

Met Asn Tyr Arg Gln Thr Arg His Glu Asn Val Val Leu Phe Met Gly
    610             615                 620

Ala Cys Met Asn Pro Pro His Leu Ala Ile Ile Thr Ser Phe Cys Lys
625             630                 635                     640

Gly Arg Thr Leu His Ser Phe Val Arg Asp Pro Lys Thr Ser Leu Asp
                645             650                 655

Ile Asn Lys Thr Arg Gln Ile Ala Gln Glu Ile Ile Lys Gly Met Gly
            660             665                 670

Tyr Leu His Ala Lys Gly Ile Val His Lys Asp Leu Lys Ser Lys Asn
        675             680                 685

Val Phe Tyr Asp Asn Gly Lys Val Val Ile Thr Asp Phe Gly Leu Phe
    690             695                 700
```

-continued

```
Gly Ile Ser Gly Val Val Arg Glu Glu Arg Arg Glu Asn Gln Leu Lys
705             710                 715                 720

Leu Ser His Asp Trp Leu Cys Tyr Leu Ala Pro Glu Ile Val Arg Glu
            725                 730                 735

Met Ile Pro Gly Arg Asp Glu Asp Gln Leu Pro Phe Ser Lys Ala Ala
            740                 745                 750

Asp Val Tyr Ala Phe Gly Thr Val Trp Tyr Glu Leu Gln Ala Arg Asp
            755                 760                 765

Trp Pro Phe Lys His Gln Pro Ala Glu Ala Leu Ile Trp Gln Ile Gly
    770                 775                 780

Ser Gly Glu Gly Val Arg Arg Val Leu Ala Ser Val Ser Leu Gly Lys
785             790                 795                 800

Glu Val Gly Glu Ile Leu Ser Ala Cys Trp Ala Phe Asp Leu Gln Glu
                805                 810                 815

Arg Pro Ser Phe Ser Leu Leu Met Asp Met Leu Glu Arg Leu Pro Lys
            820                 825                 830

Leu Asn Arg Arg Leu Ser His Pro Gly His Phe Trp Lys Ser Ala Asp
        835                 840                 845

Ile Asn Ser Ser Lys Val Met Pro Arg Phe Glu Arg Phe Gly Leu Gly
850                 855                 860

Thr Leu Glu Ser Gly Asn Pro Lys Met
865             870
```

( 2 ) INFORMATION FOR SEQ ID NO:7:

( i ) SEQUENCE CHARACTERISTICS:
      ( A ) LENGTH: 2846 base pairs
      ( B ) TYPE: nucleic acid
      ( C ) STRANDEDNESS: double
      ( D ) TOPOLOGY: linear ( i i ) MOLECULE TYPE: cDNA ( x i ) SEQUENCE DESCRIPTION: SEQ ID NO:7:

```
AGAGCAGCGC TGCGCTCGGC CGCGTTGGGA GAGAAGAAGG AGGGCGGTGG CGGGGGTGAC      60
GCGGCTATCG CGGAGGGAGG TGCAGGGGCC GCGGCCAGCC GGACACTGCA GCAGTGCGGG     120
CAGCTGCAGA AGCTCATCGA CATCTCCATC GGCAGCCTGC GCGGGCTGCG CACCAAGTGC     180
GTGGTGTCCA ACGACCTCAC CCAGCAGGAG ATACGGACCC TGGAGGCGAA GCTGGTCCGT     240
TACATTTGTA AGCAGAGGCA GTGCAAGCTG AGCGTGGCTC CCGGTGAGAG GACCCCAGAG     300
CTCAACAGCT ACCCCGCTT CAGCGACTGG CTGTACACTT TCAACGTGAG GCCGGAGGTG      360
GTGCAGGAGA TCCCCCGAGA CCTCACGCTG GATGCCCTGC TGGAGATGAA TGAGGCCAAG     420
GTGAAGGAGA CGCTGCGGCG CTGTGGGGCC AGCGGGGATG AGTGTGGCCG TCTGCAGTAT     480
GCCCTCACCT GCCTGCGGAA GGTGACAGGC CTGGGAGGG AGCACAAGGA GGACTCCAGT      540
TGGAGTTCAT TGGATGCGCG GCGGGAAAGT GGCTCAGGGC CTTCCACGGA CACCCTCTCA     600
GCAGCCAGCC TGCCCTGGCC CCCAGGGAGC TCCAGCTGG GCAGAGCAGG CAACAGCGCC      660
CAGGGCCCAC GCTCCATCTC CGTGTCAGCT CTTCCCGCCT CAGACTCCCC CACCCCCAGC     720
TTCAGTGAGG GCCTCTCAGA CACCTGTATT CCCCTGCACG CCAGCGGCCG GCTGACCCCC     780
CGTGCCCTGC ACAGCTTCAT CACCCCGCCC ACCACACCCC AGCTGCGACG GCACACCAAG     840
CTGAAGCCAC CACGGACGCC CCCCCCACCC AGCCGCAAGG TCTTCCAGCT GCTGCCCAGC     900
TTCCCCACAC TCACCCGGAG CAAGTCCCAT GAGTCTCAGC TGGGGAACCG CATTGATGAC    960
GTCTCCTCGA TGAGGTTTGA TCTCTCGCAT GGATCCCCAC AGATGGTACG GAGGGATATC   1020
```

| | | | | | |
|---|---|---|---|---|---|
| GGGCTGTCGG | TGACGCACAG | GTTCTCCACC | AAGTCCTGGC | TGTCGCAGGT | CTGCCACGTG | 1080 |
| TGCCAGAAGA | GCATGATATT | TGGAGTGAAG | TGCAAGCATT | GCAGGTTGAA | GTGTCACAAC | 1140 |
| AAATGTACCA | AAGAAGCCCC | TGCCTGTAGA | ATATCCTTCC | TGCCACTAAC | TCGGCTTCGG | 1200 |
| AGGACAGAAT | CTGTCCCCTC | GGACATCAAC | AACCCGGTGG | ACAGAGCAGC | CGAACCCCAT | 1260 |
| TTTGGAACCC | TCCCCAAAGC | ACTGACAAAG | AAGGAGCACC | CTCCGGCCAT | GAATCACCTG | 1320 |
| GACTCCAGCA | GCAACCCTTC | CTCCACCACC | TCCTCCACAC | CCTCCTCACC | GGCGCCCTTC | 1380 |
| CCGACATCAT | CCAACCCATC | CAGCGCCACC | ACGCCCCCA | ACCCCTCACC | TGGCCAGCGG | 1440 |
| GACAGCAGGT | TCAACTTCCC | AGCTGCCTAC | TTCATTCATC | ATAGACAGCA | GTTTATCTTT | 1500 |
| CCAGACATTT | CAGCCTTTGC | ACACGCAGCC | CCGCTCCCTG | AAGCTGCCGA | CGGTACCCGG | 1560 |
| CTCGATGACC | AGCCGAAAGC | AGATGTGTTG | GAAGCTCACG | AAGCGGAGGC | TGAGGAGCCA | 1620 |
| GAGGCTGGCA | AGTCAGAGGC | AGAAGACGAT | GAGGACGAGG | TGGACGACTT | GCCGAGCTCT | 1680 |
| CGCCGGCCCT | GGCGGGGCCC | CATCTCTCGC | AAGGCCAGCC | AGACCAGCGT | GTACCTGCAG | 1740 |
| GAGTGGGACA | TCCCCTTCGA | GCAGGTAGAG | CTGGGCGAGC | CCATCGGGCA | GGGCCGCTGG | 1800 |
| GGCCGGGTGC | ACCGCGGCCG | CTGGCATGGC | GAGGTGGCCA | TTCGCCTGCT | GGAGATGGAC | 1860 |
| GGCCACAACC | AGGACCACCT | GAAGCTCTTC | AAGAAGAGG | TGATGAACTA | CCGGCAGACG | 1920 |
| CGGCATGAGA | ACGTGGTGCT | CTTCATGGGG | GCCTGCATGA | ACCCGCCCCA | CCTGGCCATT | 1980 |
| ATCACCAGCT | TCTGCAAGGG | GCGGACGTTG | CACTCGTTTG | TGAGGGACCC | CAAGACGTCT | 2040 |
| CTGGACATCA | ACAAGACGAG | GCAAATCGCT | CAGGAGATCA | TCAAGGGCAT | GGATATCTT | 2100 |
| CATGCCAAGG | GCATCGTACA | CAAAGATCTC | AAATCTAAGA | ACGTCTTCTA | TGACAACGGC | 2160 |
| AAGGTGGTCA | TCACAGACTT | CGGGCTGTTT | GGGATCTCAG | GCGTGGTCCG | AGAGGGACGG | 2220 |
| CGTGAGAACC | AGCTAAAGCT | GTCCCACGAC | TGGCTGTGCT | ATCTGGCCCC | TGAGATTGTA | 2280 |
| CGCGAGATGA | CCCCCGGGAA | GGACGAGGAT | CAGCTGCCAT | TCTCCAAAGC | TGCTGATGTC | 2340 |
| TATGCATTTG | GGACTGTTTG | GTATGAGCTG | CAAGCAAGAG | ACTGGCCCTT | GAAGAACCAG | 2400 |
| GCTGCAGAGG | CATCCATCTG | GCAGATTGGA | AGCGGGGAAG | GAATGAAGCG | TGTCCTGACT | 2460 |
| TCTGTCAGCT | TGGGGAAGGA | AGTCAGTGAG | ATCCTGTCGG | CCTGCTGGGC | TTTCGACCTG | 2520 |
| CAGGAGAGAC | CCAGCTTCAG | CCTGCTGATG | GACATGCTGG | AGAAACTTCC | CAAGCTGAAC | 2580 |
| CGGCGGCTCT | CCCACCCTGG | ACACTTCTGG | AAGTCAGCTG | AGTTGTAGGC | CTGGCTGCCT | 2640 |
| TGCATGCACC | AGGGGCTTTC | TTCCTCCTAA | TCAACAACTC | AGCACCGTGA | CTTCTGCTAA | 2700 |
| AATGCAAAAT | GAGATGCGGG | CACTAACCCA | GGGGATGCCA | CCTCTGCTGC | TCCAGTCGTC | 2760 |
| TCTCTCGAGG | CTACTTCTTT | TGCTTTGTTT | TAAAAACTGG | CCCTCTGCCC | TCTCCACGTG | 2820 |
| GCCTGCATAT | GCCCAAGCCG | GAATTC | | | | 2846 |

( 2 ) INFORMATION FOR SEQ ID NO:8:

( i ) SEQUENCE CHARACTERISTICS:
( A ) LENGTH: 875 amino acids
( B ) TYPE: amino acid
( C ) STRANDEDNESS: Not Relevant
( D ) TOPOLOGY: Not Relevant ( i i ) MOLECULE TYPE: peptide ( x i ) SEQUENCE DESCRIPTION: SEQ ID NO:8:

Arg Ala Ala Leu Arg Ser Ala Ala Leu Gly Glu Lys Lys Glu Gly Gly
1               5                   10                  15

Gly Gly Gly Asp Ala Ala Ile Ala Glu Gly Gly Ala Gly Ala Ala Ala

```
                         20                          25                          30
    Ser  Arg  Thr  Leu  Gln  Gln  Cys  Gly  Gln  Leu  Gln  Lys  Leu  Ile  Asp  Ile
              35                        40                        45
    Ser  Ile  Gly  Ser  Leu  Arg  Gly  Leu  Arg  Thr  Lys  Cys  Val  Val  Ser  Asn
         50                        55                        60
    Asp  Leu  Thr  Gln  Gln  Glu  Ile  Arg  Thr  Leu  Glu  Ala  Lys  Leu  Val  Arg
    65                       70                        75                        80
    Tyr  Ile  Cys  Lys  Gln  Arg  Gln  Cys  Lys  Leu  Ser  Val  Ala  Pro  Gly  Glu
                   85                        90                        95
    Arg  Thr  Pro  Glu  Leu  Asn  Ser  Tyr  Pro  Arg  Phe  Ser  Asp  Trp  Leu  Tyr
                   100                       105                       110
    Thr  Phe  Asn  Val  Arg  Pro  Glu  Val  Gln  Glu  Ile  Pro  Arg  Asp  Leu
              115                       120                       125
    Thr  Leu  Asp  Ala  Leu  Leu  Glu  Met  Asn  Glu  Ala  Lys  Val  Lys  Glu  Thr
              130                       135                       140
    Leu  Arg  Arg  Cys  Gly  Ala  Ser  Gly  Asp  Glu  Cys  Gly  Arg  Leu  Gln  Tyr
    145                       150                       155                       160
    Ala  Leu  Thr  Cys  Leu  Arg  Lys  Val  Thr  Leu  Gly  Gly  Glu  His  Lys
                   165                       170                       175
    Glu  Asp  Ser  Ser  Trp  Ser  Ser  Leu  Asp  Ala  Arg  Arg  Glu  Ser  Gly  Ser
                   180                       185                       190
    Gly  Pro  Ser  Thr  Asp  Thr  Leu  Ser  Ala  Ala  Ser  Leu  Pro  Trp  Pro  Pro
                   195                       200                       205
    Gly  Ser  Ser  Gln  Leu  Gly  Arg  Ala  Gly  Asn  Ser  Ala  Gln  Gly  Pro  Arg
         210                       215                       220
    Ser  Ile  Ser  Val  Ser  Ala  Leu  Pro  Ala  Ser  Asp  Ser  Pro  Thr  Pro  Ser
    225                       230                       235                       240
    Phe  Ser  Glu  Gly  Leu  Ser  Asp  Thr  Cys  Ile  Pro  Leu  His  Ala  Ser  Gly
                   245                       250                       255
    Arg  Leu  Thr  Pro  Arg  Ala  Leu  His  Ser  Phe  Ile  Thr  Pro  Thr  Thr
                   260                       265                       270
    Pro  Gln  Leu  Arg  Arg  His  Thr  Lys  Leu  Lys  Pro  Pro  Arg  Thr  Pro  Pro
              275                       280                       285
    Pro  Pro  Ser  Arg  Lys  Val  Phe  Gln  Leu  Leu  Pro  Ser  Phe  Pro  Thr  Leu
    290                       295                       300
    Thr  Arg  Ser  Lys  Ser  His  Glu  Ser  Gln  Leu  Gly  Asn  Arg  Ile  Asp  Asp
    305                       310                       315                       320
    Val  Ser  Ser  Met  Arg  Phe  Asp  Leu  Ser  His  Gly  Ser  Pro  Gln  Met  Val
                   325                       330                       335
    Arg  Arg  Asp  Ile  Gly  Leu  Ser  Val  Thr  His  Arg  Phe  Ser  Thr  Lys  Ser
                   340                       345                       350
    Trp  Leu  Ser  Gln  Val  Cys  His  Val  Cys  Gln  Lys  Ser  Met  Ile  Phe  Gly
              355                       360                       365
    Val  Lys  Cys  Lys  His  Cys  Arg  Leu  Lys  Cys  His  Asn  Lys  Cys  Thr  Lys
         370                       375                       380
    Glu  Ala  Pro  Ala  Cys  Arg  Ile  Ser  Phe  Leu  Pro  Leu  Thr  Arg  Leu  Arg
    385                       390                       395                       400
    Arg  Thr  Glu  Ser  Val  Pro  Ser  Asp  Ile  Asn  Asn  Pro  Val  Asp  Arg  Ala
                   405                       410                       415
    Ala  Glu  Pro  His  Phe  Gly  Thr  Leu  Pro  Lys  Ala  Leu  Thr  Lys  Lys  Glu
                   420                       425                       430
    His  Pro  Pro  Ala  Met  Asn  His  Leu  Asp  Ser  Ser  Asn  Pro  Ser  Ser
                   435                       440                       445
```

```
Thr Thr Ser Ser Thr Pro Ser Ser Pro Ala Pro Phe Pro Thr Ser Ser
    450             455             460
Asn Pro Ser Ser Ala Thr Pro Pro Asn Pro Ser Pro Gly Gln Arg
465             470             475                 480
Asp Ser Arg Phe Asn Phe Pro Ala Ala Tyr Phe Ile His His Arg Gln
            485             490                 495
Gln Phe Ile Phe Pro Asp Ile Ser Ala Phe Ala His Ala Ala Pro Leu
            500             505             510
Pro Glu Ala Ala Asp Gly Thr Arg Leu Asp Asp Gln Pro Lys Ala Asp
            515             520             525
Val Leu Glu Ala His Glu Ala Glu Glu Pro Glu Ala Gly Lys
    530             535             540
Ser Glu Ala Glu Asp Asp Glu Asp Glu Val Asp Asp Leu Pro Ser Ser
545             550             555                 560
Arg Arg Pro Trp Arg Gly Pro Ile Ser Arg Lys Ala Ser Gln Thr Ser
            565             570             575
Val Tyr Leu Gln Glu Trp Asp Ile Pro Phe Glu Gln Val Glu Leu Gly
            580             585             590
Glu Pro Ile Gly Gln Gly Arg Trp Gly Arg Val His Arg Gly Arg Trp
        595             600             605
His Gly Glu Val Ala Ile Arg Leu Leu Glu Met Asp Gly His Asn Gln
    610             615             620
Asp His Leu Lys Leu Phe Lys Lys Glu Val Met Asn Tyr Arg Gln Thr
625             630             635                 640
Arg His Glu Asn Val Val Leu Phe Met Gly Ala Cys Met Asn Pro Pro
            645             650             655
His Leu Ala Ile Ile Thr Ser Phe Cys Lys Gly Arg Thr Leu His Ser
            660             665             670
Phe Val Arg Asp Pro Lys Thr Ser Leu Asp Ile Asn Lys Thr Arg Gln
        675             680             685
Ile Ala Gln Glu Ile Ile Lys Gly Met Gly Tyr Leu His Ala Lys Gly
    690             695             700
Ile Val His Lys Asp Leu Lys Ser Lys Asn Val Phe Tyr Asp Asn Gly
705             710             715                 720
Lys Val Val Ile Thr Asp Phe Gly Leu Phe Gly Ile Ser Gly Val Val
            725             730             735
Arg Glu Gly Arg Arg Glu Asn Gln Leu Lys Leu Ser His Asp Trp Leu
        740             745             750
Cys Tyr Leu Ala Pro Glu Ile Val Arg Glu Met Thr Pro Gly Lys Asp
    755             760             765
Glu Asp Gln Leu Pro Phe Ser Lys Ala Ala Asp Val Tyr Ala Phe Gly
770             775             780
Thr Val Trp Tyr Glu Leu Gln Ala Arg Asp Trp Pro Leu Lys Asn Gln
785             790             795                 800
Ala Ala Glu Ala Ser Ile Trp Gln Ile Gly Ser Gly Glu Gly Met Lys
            805             810             815
Arg Val Leu Thr Ser Val Ser Leu Gly Lys Glu Val Ser Glu Ile Leu
        820             825             830
Ser Ala Cys Trp Ala Phe Asp Leu Gln Glu Arg Pro Ser Phe Ser Leu
    835             840             845
Leu Met Asp Met Leu Glu Lys Leu Pro Lys Leu Asn Arg Arg Leu Ser
850             855             860
His Pro Gly His Phe Trp Lys Ser Ala Glu Leu
865             870             875
```

( 2 ) INFORMATION FOR SEQ ID NO:9:

( i ) SEQUENCE CHARACTERISTICS:
        ( A ) LENGTH: 2126 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:9:

```
GAATTCCGGC ACACATCAGC ACTCACACAG CACACAGCAC ACACACAGCA CACATCAGCG      60
CACACACAGC ACAGCTTCAT CACCCCGCCC ACCACACCCC AGCTGCGACG GCACACCAAG     120
CTGAAGCCAC CACGGACGCC CCCCCCACCC AGCCGCAAGG TCTTCCAGCT GCTGCCCAGC     180
TTCCCCACAC TCACCCGGAG CAAGTCCCAT GAGTCTCAGC TGGGGAACCG CATTGATGAC     240
GTCTCCTCGA TGAGGTTTGA TCTCTCGCAT GGATCCCCAC AGATGGTACG GAGGGATATC     300
GGGCTGTCGG TGACGCACAG GTTCTCCACC AAGTCCTGGC TGTCGCAGGT CTGCCACGTG     360
TGCCAGAAGA GCATGATATT TGGAGTGAAG TGCAAGCATT GCAGGTTGAA GTGTCACAAC     420
AAATGTACCA AAGAAGCCCC TGCCTGTAGA ATATCCTTCC TGCCACTAAC TCGGCTTCGG     480
AGGACAGAAT CTGTCCCCTC GGACATCAAC AACCCGGTGG ACAGAGCAGC CGAACCCCAT     540
TTTGGAACCC TCCCCAAAGC ACTGACAAAG AAGGAGCACC CTCCGGCCAT GAATCACCTG     600
GACTCCAGCA GCAACCCTTC CTCCACCACC TCCTCCACAC CCTCCTCACC GGCGCCCTTC     660
CCGACATCAT CCAACCCATC CAGCGCCACC ACGCCCCCA ACCCCTCACC TGGCCAGCGG      720
GACAGCAGGT TCAACTTCCC AGCTGCCTAC TTCATTCATC ATAGACAGCA GTTTATCTTT     780
CCAGACATTT CAGCCTTTGC ACACGCAGCC CCGCTCCCTG AAGCTGCCGA CGGTACCCGG     840
CTCGATGACC AGCCGAAAGC AGATGTGTTG GAAGCTCACG AAGCGGAGGC TGAGGAGCCA     900
GAGGCTGGCA AGTCAGAGGC AGAAGACGAT GAGGACGAGG TGGACGACTT GCCGAGCTCT     960
CGCCGGCCCT GGCGGGGCCC CATCTCTCGC AAGGCCAGCC AGACCAGCGT GTACCTGCAG    1020
GAGTGGGACA TCCCCTTCGA GCAGGTAGAG CTGGGCGAGC CCATCGGGCA GGGCCGCTGG    1080
GGCCGGGTGC ACCGCGGCCG CTGGCATGGC GAGGTGGCCA TTCGCCTGCT GGAGATGGAC    1140
GGCCACAACC AGGACCACCT GAAGCTCTTC AAGAAAGAGG TGATGAACTA CCGGCAGACG    1200
CGGCATGAGA ACGTGGTGCT CTTCATGGGG GCCTGCATGA ACCCGCCCCA CCTGGCCATT    1260
ATCACCAGCT TCTGCAAGGG GCGGACGTTG CACTCGTTTG TGAGGGACCC CAAGACGTCT    1320
CTGGACATCA ACAAGACGAG GCAAATCGCT CAGGAGATCA TCAAGGGCAT GGGATATCTT    1380
CATGCCAAGG GCATCGTACA CAAAGATCTC AAATCTAAGA ACGTCTTCTA TGACAACGGC    1440
AAGGTGGTCA TCACAGACTT CGGGCTGTTT GGGATCTCAG GCGTGGTCCG AGAGGGACGG    1500
CGTGAGAACC AGCTAAAGCT GTCCACGAC TGGCTGTGCT ATCTGGCCCC TGAGATTGTA     1560
CGCGAGATGA CCCCCGGGAA GGACGAGGAT CAGCTGCCAT TCTCCAAAGC TGCTGATGTC    1620
TATGCATTTG GGACTGTTTG GTATGAGCTG CAAGCAAGAG ACTGGCCCTT GAAGAACCAG    1680
GCTGCAGAGG CATCCATCTG GCAGATTGGA AGCGGGGAAG GAATGAAGCG TGTCCTGACT    1740
TCTGTCAGCT TGGGGAAGGA AGTCAGTGAG ATCCTGTCGG CCTGCTGGGC TTTCGACCTG    1800
CAGGAGAGAC CCAGCTTCAG CCTGCTGATG GACATGCTGG AGAAACTTCC CAAGCTGAAC    1860
CGGCGGCTCT CCCACCCTGG ACACTTCTGG AAGTCAGCTG AGTTGTAGGC CTGGCTGCCT    1920
TGCATGCACC AGGGGCTTTC TTCCTCCTAA TCAACAACTC AGCACCGTGA CTTCTGCTAA    1980
```

-continued

```
AATGCAAAAT GAGATGCGGG CACTAACCCA GGGGATGCCA CCTCTGCTGC TCCAGTCGTC  2040

TCTCTCGAGG CTACTTCTTT TGCTTTGTTT TAAAAACTGG CCCTCTGCCC TCTCCACGTG  2100

GCCTGCATAT GCCCAAGCCG GAATTC                                      2126
```

( 2 ) INFORMATION FOR SEQ ID NO:10:

( i ) SEQUENCE CHARACTERISTICS:
        ( A ) LENGTH: 635 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:10:

```
Glu Phe Arg His Thr Ser Ala Leu Thr Gln His Thr Ala His Thr Gln
1               5                   10                  15

His Thr Ser Ala His Thr Gln His Ser Phe Ile Thr Pro Pro Thr Thr
            20                  25                  30

Pro Gln Leu Arg Arg His Thr Lys Leu Lys Pro Pro Arg Thr Pro Pro
        35                  40                  45

Pro Pro Ser Arg Lys Val Phe Gln Leu Leu Pro Ser Phe Pro Thr Leu
    50                  55                  60

Thr Arg Ser Lys Ser His Glu Ser Gln Leu Gly Asn Arg Ile Asp Asp
65                  70                  75                  80

Val Ser Ser Met Arg Phe Asp Leu Ser His Gly Ser Pro Gln Met Val
                85                  90                  95

Arg Arg Asp Ile Gly Leu Ser Val Thr His Arg Phe Ser Thr Lys Ser
            100                 105                 110

Trp Leu Ser Gln Val Cys His Val Cys Gln Lys Ser Met Ile Phe Gly
        115                 120                 125

Val Lys Cys Lys His Cys Arg Leu Lys Cys His Asn Lys Cys Thr Lys
    130                 135                 140

Glu Ala Pro Ala Cys Arg Ile Ser Phe Leu Pro Leu Thr Arg Leu Arg
145                 150                 155                 160

Arg Thr Glu Ser Val Pro Ser Asp Ile Asn Asn Pro Val Asp Arg Ala
                165                 170                 175

Ala Glu Pro His Phe Gly Thr Leu Pro Lys Ala Leu Thr Lys Lys Glu
            180                 185                 190

His Pro Pro Ala Met Asn His Leu Asp Ser Ser Ser Asn Pro Ser Ser
        195                 200                 205

Thr Thr Ser Ser Thr Pro Ser Ser Pro Ala Pro Phe Pro Thr Ser Ser
    210                 215                 220

Asn Pro Ser Ser Ala Thr Thr Pro Pro Asn Pro Ser Pro Gly Gln Arg
225                 230                 235                 240

Asp Ser Arg Phe Asn Phe Pro Ala Ala Tyr Phe Ile His His Arg Gln
                245                 250                 255

Gln Phe Ile Phe Pro Asp Ile Ser Ala Phe Ala His Ala Ala Pro Leu
            260                 265                 270

Pro Glu Ala Ala Asp Gly Thr Arg Leu Asp Asp Gln Pro Lys Ala Asp
        275                 280                 285

Val Leu Glu Ala His Glu Ala Glu Ala Glu Glu Pro Glu Ala Gly Lys
    290                 295                 300

Ser Glu Ala Glu Asp Asp Glu Asp Glu Val Asp Asp Leu Pro Ser Ser
305                 310                 315                 320

Arg Arg Pro Trp Arg Gly Pro Ile Ser Arg Lys Ala Ser Gln Thr Ser
```

|     |     |     |     |     | 325 |     |     |     |     | 330 |     |     |     |     | 335 |     |
| --- | --- | --- | --- | --- | --- | --- | --- | --- | --- | --- | --- | --- | --- | --- | --- | --- |

Val Tyr Leu Gln Glu Trp Asp Ile Pro Phe Glu Gln Val Glu Leu Gly
                340                 345                 350

Glu Pro Ile Gly Gln Gly Arg Trp Gly Arg Val His Arg Gly Arg Trp
            355                 360                 365

His Gly Glu Val Ala Ile Arg Leu Leu Glu Met Asp Gly His Asn Gln
        370                 375             380

Asp His Leu Lys Leu Phe Lys Lys Glu Val Met Asn Tyr Arg Gln Thr
385                 390                 395                 400

Arg His Glu Asn Val Val Leu Phe Met Gly Ala Cys Met Asn Pro Pro
                405             410             415

His Leu Ala Ile Ile Thr Ser Phe Cys Lys Gly Arg Thr Leu His Ser
            420             425             430

Phe Val Arg Asp Pro Lys Thr Ser Leu Asp Ile Asn Lys Thr Arg Gln
        435             440             445

Ile Ala Gln Glu Ile Ile Lys Gly Met Gly Tyr Leu His Ala Lys Gly
    450             455             460

Ile Val His Lys Asp Leu Lys Ser Lys Asn Val Phe Tyr Asp Asn Gly
465             470             475             480

Lys Val Val Ile Thr Asp Phe Gly Leu Phe Gly Ile Ser Gly Val Val
                485             490             495

Arg Glu Gly Arg Arg Glu Asn Gln Leu Lys Leu Ser His Asp Trp Leu
            500             505             510

Cys Tyr Leu Ala Pro Glu Ile Val Arg Glu Met Thr Pro Gly Lys Asp
        515             520             525

Glu Asp Gln Leu Pro Phe Ser Lys Ala Ala Asp Val Tyr Ala Phe Gly
    530             535             540

Thr Val Trp Tyr Glu Leu Gln Ala Arg Asp Trp Pro Leu Lys Asn Gln
545             550             555             560

Ala Ala Glu Ala Ser Ile Trp Gln Ile Gly Ser Gly Glu Gly Met Lys
            565             570             575

Arg Val Leu Thr Ser Val Ser Leu Gly Lys Glu Val Ser Glu Ile Leu
        580             585             590

Ser Ala Cys Trp Ala Phe Asp Leu Gln Glu Arg Pro Ser Phe Ser Leu
    595             600             605

Leu Met Asp Met Leu Glu Lys Leu Pro Lys Leu Asn Arg Arg Leu Ser
    610             615             620

His Pro Gly His Phe Trp Lys Ser Ala Glu Leu
625             630             635

( 2 ) INFORMATION FOR SEQ ID NO:11:

( i ) SEQUENCE CHARACTERISTICS:
    ( A ) LENGTH: 326 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:11:

Asp Ala Lys Ser Ser Glu Glu Asn Trp Asn Ile Leu Ala Glu Glu Ile
1               5                   10                  15

Leu Ile Gly Pro Arg Ile Gly Ser Gly Ser Phe Gly Thr Val Tyr Arg
            20                  25                  30

Ala His Trp His Gly Pro Val Pro Val Lys Thr Leu Asn Val Lys Thr
        35                  40                  45

```
Pro  Ser  Pro  Ala  Gln  Leu  Gln  Ala  Phe  Lys  Asn  Glu  Val  Ala  Met  Leu
     50                  55                       60

Lys  Lys  Thr  Arg  His  Cys  Asn  Ile  Leu  Ile  Phe  Met  Gly  Cys  Val  Ser
65                       70                       75                            80

Lys  Pro  Ser  Leu  Ala  Ile  Val  Thr  Gln  Trp  Cys  Glu  Gly  Ser  Ser  Leu
                    85                       90                            95

Tyr  Lys  His  Val  His  Val  Ser  Glu  Thr  Lys  Phe  Lys  Leu  Asn  Thr  Leu
               100                      105                      110

Ile  Asp  Ile  Gly  Arg  Gln  Val  Ala  Gln  Gln  Met  Asp  Tyr  Leu  His  Ala
          115                      120                      125

Lys  Asn  Ile  Ile  His  Arg  Asp  Leu  Lys  Ser  Asn  Asn  Ile  Phe  Leu  His
     130                      135                      140

Glu  Asp  Leu  Ser  Val  Lys  Ile  Gly  Asp  Phe  Gly  Leu  Ala  Thr  Ala  Lys
145                      150                      155                           160

Thr  Arg  Trp  Ser  Gly  Glu  Lys  Gln  Ala  Asn  Gln  Pro  Thr  Gly  Ser  Ile
               165                      170                      175

Leu  Trp  Met  Ala  Pro  Glu  Val  Ile  Arg  Met  Gln  Glu  Leu  Asn  Pro  Tyr
               180                      185                      190

Ser  Phe  Gln  Ser  Asp  Val  Tyr  Ala  Phe  Gly  Ile  Val  Met  Tyr  Glu  Leu
          195                      200                      205

Leu  Ala  Glu  Cys  Leu  Pro  Tyr  Gly  His  Ile  Ser  Asn  Lys  Asp  Gln  Ile
     210                      215                      220

Leu  Phe  Met  Val  Gly  Arg  Gly  Leu  Leu  Arg  Pro  Asp  Met  Ser  Gln  Val
225                      230                      235                           240

Arg  Ser  Asp  Ala  Arg  Arg  His  Ser  Lys  Arg  Ile  Ala  Glu  Asp  Cys  Ile
               245                      250                      255

Lys  Tyr  Thr  Pro  Lys  Asp  Arg  Pro  Leu  Phe  Arg  Pro  Leu  Leu  Trp  Met
               260                      265                      270

Leu  Glu  Asn  Met  Leu  Arg  Thr  Leu  Pro  Lys  Ile  His  Arg  Ser  Ala  Ser
          275                      280                      285

Glu  Pro  Asn  Leu  Thr  Gln  Ser  Gln  Leu  Gln  Asn  Asp  Glu  Phe  Leu  Tyr
     290                      295                      300

Leu  Pro  Ser  Pro  Lys  Thr  Pro  Val  Asn  Phe  Asn  Asn  Phe  Gln  Phe  Phe
305                      310                      315                           320

Gly  Ser  Ala  Gly  Asn  Ile
               325
```

( 2 ) INFORMATION FOR SEQ ID NO:12:

( i ) SEQUENCE CHARACTERISTICS:
      ( A ) LENGTH: 315 amino acids
      ( B ) TYPE: amino acid
      ( C ) STRANDEDNESS: Not Relevant
      ( D ) TOPOLOGY: Not Relevant ( i i ) MOLECULE TYPE: peptide ( x i ) SEQUENCE DESCRIPTION: SEQ ID NO:12:

```
Gly  Gln  Arg  Asp  Ser  Ser  Tyr  Tyr  Trp  Glu  Ile  Glu  Ala  Ser  Glu  Val
1                   5                   10                       15

Met  Leu  Ser  Thr  Arg  Ile  Gly  Ser  Gly  Ser  Phe  Gly  Thr  Val  Tyr  Lys
               20                  25                       30

Cys  Lys  Trp  His  Gly  Asp  Val  Ala  Val  Lys  Ile  Leu  Lys  Val  Val  Asp
               35                  40                       45

Pro  Thr  Pro  Glu  Gln  Phe  Gln  Ala  Phe  Arg  Asn  Glu  Val  Ala  Val  Leu
     50                  55                       60
```

-continued

| | | | | | | | | | | | | | | | |
|---|---|---|---|---|---|---|---|---|---|---|---|---|---|---|---|
| Arg 65 | Lys | Thr | Arg | His | Val 70 | Asn | Ile | Leu | Phe 75 | Met | Gly | Tyr | Met | Thr 80 |
| Lys | Asp | Asn | Leu | Ala 85 | Ile | Val | Thr | Gln | Trp 90 | Cys | Glu | Gly | Ser | Ser 95 | Leu |
| Tyr | Lys | His | Leu 100 | His | Val | Gln | Glu | Thr 105 | Lys | Phe | Gln | Met | Phe 110 | Gln | Leu |
| Ile | Asp | Ile 115 | Ala | Arg | Gln | Thr | Ala 120 | Gln | Gly | Met | Asp | Tyr 125 | Leu | His | Ala |
| Lys | Asn 130 | Ile | Ile | His | Arg | Asp 135 | Met | Lys | Ser | Asn | Asn 140 | Ile | Phe | Leu | His |
| Glu 145 | Gly | Leu | Thr | Val | Lys 150 | Ile | Gly | Asp | Phe | Gly 155 | Leu | Ala | Thr | Val | Lys 160 |
| Ser | Arg | Trp | Ser | Gly 165 | Ser | Gln | Gln | Val | Glu 170 | Gln | Pro | Thr | Gly | Ser 175 | Val |
| Leu | Trp | Met | Ala 180 | Pro | Glu | Val | Ile | Arg 185 | Met | Gln | Asp | Asn | Asn 190 | Pro | Phe |
| Ser | Phe | Gln 195 | Ser | Asp | Val | Tyr | Ser 200 | Tyr | Gly | Ile | Val | Leu 205 | Tyr | Glu | Leu |
| Met | Thr 210 | Gly | Glu | Leu | Pro | Tyr 215 | Ser | His | Ile | Asn | Asn 220 | Arg | Asp | Gln | Ile |
| Ile 225 | Phe | Met | Val | Gly | Arg 230 | Gly | Tyr | Ala | Ser | Pro 235 | Asp | Leu | Ser | Lys | Leu 240 |
| Tyr | Lys | Asn | Cys | Pro 245 | Lys | Ala | Met | Lys | Arg 250 | Leu | Val | Ala | Asp | Cys 255 | Val |
| Lys | Lys | Val | Lys 260 | Glu | Glu | Arg | Pro | Leu 265 | Phe | Pro | Gln | Ile | Leu 270 | Ser | Ser |
| Ile | Glu | Leu 275 | Leu | Gln | His | Ser | Leu 280 | Pro | Lys | Ile | Asn | Arg 285 | Ser | Ala | Ser |
| Glu | Pro 290 | Ser | Leu | His | Arg | Ala 295 | Ala | His | Thr | Glu | Asp 300 | Ile | Asn | Ala | Cys |
| Thr 305 | Leu | Thr | Thr | Ser | Pro 310 | Arg | Leu | Pro | Val | Phe 315 | | | | | |